(12) United States Patent
Hariri

(10) Patent No.: US 7,311,905 B2
(45) Date of Patent: *Dec. 25, 2007

(54) EMBRYONIC-LIKE STEM CELLS DERIVED FROM POST-PARTUM MAMMALIAN PLACENTA, AND USES AND METHODS OF TREATMENT USING SAID CELLS

(75) Inventor: Robert J. Hariri, Florham Park, NJ (US)

(73) Assignee: Anthrogenesis Corporation, Summit, NJ (US)

( * ) Notice: Subject to any disclaimer, the term of this patent is extended or adjusted under 35 U.S.C. 154(b) by 324 days.

This patent is subject to a terminal disclaimer.

(21) Appl. No.: 10/366,671

(22) Filed: Feb. 13, 2003

(65) Prior Publication Data

US 2003/0180269 A1 Sep. 25, 2003

Related U.S. Application Data

(63) Continuation-in-part of application No. 10/076,180, filed on Feb. 13, 2002.

(60) Provisional application No. 60/437,292, filed on Dec. 31, 2002.

(51) Int. Cl.
*A01N 65/00* (2006.01)

(52) U.S. Cl. .................. 424/93.1; 424/583; 435/325

(58) Field of Classification Search .............. None
See application file for complete search history.

(56) References Cited

U.S. PATENT DOCUMENTS

| | | |
|---|---|---|
| 3,862,002 A | 1/1975 | Sanders |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,372,581 A | 12/1994 | Anderson |
| 5,415,665 A | 5/1995 | Hessel et al. |
| 5,437,994 A | 8/1995 | Emerson et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,635,387 A | 6/1997 | Fei et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,806,529 A | 9/1998 | Reisner et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,851,984 A | 12/1998 | Matthews et al. |
| 5,855,619 A | 1/1999 | Caplan et al. |
| 5,858,782 A | 1/1999 | Long et al. |
| 5,861,315 A | 1/1999 | Nakahata |
| 5,874,301 A | 2/1999 | Keller et al. |
| 5,877,299 A | 3/1999 | Thomas et al. |
| 5,879,318 A | 3/1999 | Van Der Heiden et al. |

(Continued)

FOREIGN PATENT DOCUMENTS

CN 1548529 5/2003

(Continued)

OTHER PUBLICATIONS

Liu et al, Bone Marrow Transplant 1999;24:247-52.*

(Continued)

*Primary Examiner*—Q. Janice Li
(74) *Attorney, Agent, or Firm*—Jones Day

(57) ABSTRACT

The present invention provides compositions and methods of using embryonic-like stem cells that originate from a post-partum placenta with conventional cord blood compositions or other stem or progenitor cells. The embryonic-like stem cells can be used alone or in a mixture with other stem cell populations. In accordance with the present invention, the embryonic-like stem cells may be mixed with other stem cell populations, including but not limited to, umbilical cord blood, fetal and neonatal hematopoietic stem cells and progenitor cells, human stem cells and progenitor cells derived from bone marrow. The embryonic-like stem cells and the mixed populations of embryonic-like stem cells and stem cells have a multitude of uses and applications, including but not limited to, therapeutic uses for transplantation and treatment and prevention of disease, and diagnostic and research uses.

17 Claims, No Drawings

U.S. PATENT DOCUMENTS

| | | | |
|---|---|---|---|
| 5,879,940 A | 3/1999 | Torok-Storb et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Verfaillie et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Brauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,540 A | 2/2000 | Bruder et al. |
| 6,022,743 A | 2/2000 | Naughton et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,102,871 A | 8/2000 | Coe |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswell |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Mataparkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,281,012 B1 | 8/2001 | McIntosh et al. |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,368,636 B1 | 4/2002 | McIntosh et al. |
| 6,387,367 B1 | 5/2002 | Davis-Sproul et al. |
| 6,387,369 B1 | 5/2002 | Pittenger et al. |
| 6,461,645 B1 | 10/2002 | Boyse et al. |
| 6,497,875 B1 | 12/2002 | Sorrell et al. |
| 6,541,024 B1 | 4/2003 | Kadiyala et al. |
| 6,685,936 B2 | 2/2004 | McIntosh et al. |
| 6,709,864 B1 | 3/2004 | Pittenger et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 7,029,666 B2 | 4/2006 | Bruder et al. |
| 2001/0005591 A1 | 6/2001 | Qasba et al. |
| 2001/0038836 A1 | 11/2001 | During et al. |
| 2002/0028510 A1 | 3/2002 | Sanberg et al. |
| 2002/0086005 A1 | 7/2002 | Chiu et al. |
| 2002/0123141 A1 | 9/2002 | Hariri |
| 2002/0132343 A1 | 9/2002 | Lum |
| 2002/0160510 A1 | 10/2002 | Hariri |
| 2003/0044977 A1 | 3/2003 | Sakuragawa et al. |
| 2003/0161818 A1 | 8/2003 | Weiss et al. |
| 2003/0235563 A1 | 12/2003 | Strom et al. |
| 2004/0018617 A1 | 1/2004 | Hwang |
| 2004/0028660 A1 | 2/2004 | Hariri |
| 2004/0048372 A1 | 3/2004 | Hariri |
| 2004/0048796 A1 | 3/2004 | Hariri |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0171147 A1 | 9/2004 | Hariri |
| 2004/0180040 A1 | 9/2004 | Phillips et al. |
| 2004/0219136 A1 | 11/2004 | Hariri |
| 2004/0229351 A1 | 11/2004 | Rodriguez et al. |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Khim et al. |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118712 A1 | 6/2005 | Tsai et al. |
| 2005/0118715 A1 | 6/2005 | Hariri |
| 2005/0124003 A1 | 6/2005 | Atala et al. |
| 2005/0143420 A1 | 6/2005 | Moutouh-de Parseval |
| 2005/0148034 A1 | 7/2005 | Payvandi |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0276792 A1 | 12/2005 | Kaminski |
| 2005/0283844 A1 | 12/2005 | Furcht et al. |
| 2006/0008450 A1 | 1/2006 | Verfaille et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0233765 A1 | 10/2006 | Messina et al. |
| 2006/0233766 A1 | 10/2006 | Messina et al. |
| 2006/0234376 A1 | 10/2006 | Mistry et al. |

| | | | |
|---|---|---|---|
| 2006/0263337 A1 | 11/2006 | Maziarz et al. | |
| 2006/0281178 A1 | 12/2006 | Sakuragaw et al. | |

FOREIGN PATENT DOCUMENTS

| | | |
|---|---|---|
| EP | 1288293 A1 | 3/2003 |
| EP | 1384775 A1 | 1/2004 |
| EP | 1535994 A1 | 6/2005 |
| JP | 2003235549 | 12/2002 |
| JP | 2005151907 | 11/2003 |
| WO | WO 90/11354 A1 | 10/1990 |
| WO | WO 91/01140 A1 | 2/1991 |
| WO | WO 91/06667 A1 | 5/1991 |
| WO | WO 93/04169 A1 | 3/1993 |
| WO | WO 95/22611 A2 | 8/1995 |
| WO | WO 95/22611 A3 | 8/1995 |
| WO | WO 96/34035 A2 | 10/1996 |
| WO | WO 96/34035 A3 | 10/1996 |
| WO | WO 96/39101 A1 | 12/1996 |
| WO | WO 98/37903 A1 | 9/1998 |
| WO | WO 99/64566 A2 | 12/1999 |
| WO | WO99/64566 A2 | 12/1999 |
| WO | WO 00/17325 A1 | 3/2000 |
| WO | WO00/17325 A1 | 3/2000 |
| WO | WO00/27999 A2 | 5/2000 |
| WO | WO 00/27999 A2 | 5/2000 |
| WO | WO00/27999 A3 | 5/2000 |
| WO | WO 00/27999 A3 | 5/2000 |
| WO | WO00/73421 | 12/2000 |
| WO | WO 00/73421 A2 | 12/2000 |
| WO | WO 00/73421 A3 | 12/2000 |
| WO | WO 01/21767 | 3/2001 |
| WO | WO 01/93909 A2 | 12/2001 |
| WO | WO 01/93909 A3 | 12/2001 |
| WO | WO 02/46373 | 6/2002 |
| WO | WO 02/64755 | 8/2002 |
| WO | WO03/042405 | 5/2003 |
| WO | WO03/089619 | 10/2003 |
| WO | WO2005/042703 | 5/2005 |
| WO | WO2005/105992 | 11/2005 |

OTHER PUBLICATIONS

Erices et al, Brit J Haematol 2000;109:235-42.*
Pesce et al, Stem Cells 2001;19:271-8.*
Abbott, Hematol Oncol 2003;21:115-130.*
Wobus et al, Physiol Rev 2005;85:635-78.*
Huss, Stem Cells 2000;18:1-9.*
Chen, R. et al., 2000, "The Potential for the Use of Mononuclear Cells from Human Umbilical Cord Blood in the Treatment of Amyotrophic Lateral Sclerosis is SOD1 Mice," J. Med. 31(1-2):21-30.
Czarneski, J. et al., 1999, "Effects of Cord Blood Transfer on the Hematopoietic Recovery Following Sublethal Irradiation in MRL 1pr/1pr Mice," Proc. Soc. Exp. Biol. Med. 220(2):79-87.
Ende, N. et al., 2001, "Human Umbilical Cord Blood Cells Ameliorate Alzheimer's Disease in Transgenic Mice," J. Med., 32(3-4):241-7.
Ende, N. et al., 2001, "Human Umbilical Cord Blood Cells Ameliorate Huntington's Disease in Transgenic Mice," J. Med., 32(3-4):231-40.
Ende, N. et al., 2001, "Pooled Umbilical Cord Blood as a Possible Universal Donor for Marrow Reconstruction and Use in Nuclear Accidents," Life Sci. 69(13):1531-9.
Ende, N., et al., 2000, "Human Umbilical Cord Blood Effect on SOD Mice (Amyotrophic Lateral Sclerosis)" Life Sci. 67(1):53-9.
Ende, N. et al., 1999, "The Feasibility of Using Blood Bank-Stored (4 Degrees C) Cord Blood, Unmatched for HLA for Marrow Transplantation," Am. J. Clin. Pathol. 111(6):773-81.
Ende, N. et al., 1995, "The Effect of Human Cord Blood on SJL/J Mice After Chemoablation and Irradiation and Its Possible Clinical Significance," Immunol. Invest. 24(6):999-1012.

Rameshwar, P. et al., 1999, "Endogenous Hematopoietic Reconstruction Induced by Human Umbilical Cord Blood Cells in Immunocompromised Mice: Implications for Adoptive Therapy," Exp. Hematol. 27(1):176-85.
Addison et al., "Metabolism of Prednisolone by the Isolated Perfused Human Placental Lobule", J. Ster. Biochem Mol. Biol., vol. 39 No. 1, pp. 83-90 (1991).
Ashihara et al., "Successful Peripheral Blood Stem Cell Transplantation for Myelodysplastic Syndrome," Bone Marrow Transplantation 24(12:1343-1345 (1999).
Barry, 1994, "Where do all the placentas go?" Canadian Journal of Infection Control 9(1):8-10.
Belvedere et al., 2000, "Increased blood volume and CD34(+)CD38(-) progenitor cell recovery using a novel umbilical cord blood collection system," Stem Cells 18(4):245-251.
Caplan, "The Mesengenic Process," Clin. Plast. Surg. 21(3):429-435 (1994).
Cardoso et al., "Release From Quiescence of CD34+ CD38− Human Umbilical Cord Blood Cells Reveals Their Potentiality to Engraft Adults," Proc Natl Acad Sci USA 90(18):8707-8711 (1993).
CD34, Medline Mesh Database, 2004.
Cole et al., 1985, EBV-Hydradoma technique and its application to human lung cancer. In Monoclonal Antibodies and Cancer Therapy, Alan R. Liss, Inc., 77-96.
Contractor et al., 1984, "A comparison of the effects of different perfusion regimens on the structure of the isolated human placental lobule," Cell Tissue Res. 237:609-617.
Cord Blood Stem Cell, Mesh Term Database 2003.
Cote et al., 1983, Generation of human monoclonal antibodies reactive with cellular antigens. Proc Natl Acad Sci U S A. 80(7):2026-30.
Damjanov et al., 1993, Retinoic acid-induced differentiation of the developmentally pluripotent human germ cell tumor-derived cell line, NCCIT. Lab Invest. 68(2):220-32.
DeLoia et al, 1998, Effects of methotrexate on trophoblast proliferation and local immune responses. Hum Reprod. 13(4):1063-9.
Dorrel, 2000, Expansion of human cord blood CD34+CD38− cells in ex vivo culture during retroviral transduction without a corresponding increase in SCID repopulation cell (SRC) frequency: dissociation of SRC phenotype and function, Blood, 95(1):102-110.
Douay et al, 1995. Characterization of late and early hematopoietic progenitor/stem cell sensitivity to mafosfamide. Bone Marrow Transplant. 15(5):769-75.
Elchalal et al., 2000, "Postpartum unbilical cord blood collection for transplantation: a comparison of three methods," Am. J. of Obstetrics & Gyn. 182(1 Pt 1):227-232.
Emerson, 1996, Ex vivo expansion of hematopoietic precursors, progenitors and stem cells. The next generation of cellular therapeutics, Blood 87(8):3082-3088.
Ende, M. et al., "Hemapoetic Transplantation By Means of Fetal (Cord) Blood: A New Method," Va Med Mon 99:276-280 (1972).
Ende N. "Collection of Umbilical Cord Blood for Transplantation," Blood 80(6):1623-1624 (1992).
Ende, N. & Chen R., "Parkinson's Disease Mice and Human Umbilical Cord Blood," Journal of Medicine 33(1-4):173-180 (2002).
Ende, N., "Berashis Cells in Human Umbilical Cord Blood Vs. Embryonic Stem Cells," Journal of Medicine 33(1-4):167-171 (2002).
Genbacev et al. 1995,Maternal smoking inhibits early human cytotrophoblast differentiation. Reprod Toxicol. 9(3):245-55.
Gluckman et al., "Cord Blood Hematopoietic Stem Cells: Bilogy and Transplantation," In: Hematology, American Society of Hematology Education program Book, 1998, p. 1-14.
Gluckman et al., "Results of Unrelated Umbilical Cord Blood Hematipoietic Stem Cell Transplant," Transfusion Clinique et Biologique 8(3):146-154 (2001).
Hows "Status of Umbilical Cord Blood Transplantation in the Year 2001," J Clin Pathol 54(6):428-434 (2001).
Keown et al., 1990, Methods for introducing DNA into mammalian cells. Methods Enzymol. 185:527-37.

Kondo et al., "Reduced Interferon Gamma Production by Antigen-Stimulated Cord Blood Mononuclear Cells is a Risk Factor of Allergic Disorders—6-Year Follow-up Study," *Clin Exp Allergy* 28(11):1340-1344 (1998).

Korbling et al., "Peripheral Blood Stem Cell Versus Bone Marrow Allotransplantation: Does the Source of Hematopoietic Stem Cells Matter?" *Blood* 98(10):2900-2908 (2001).

Kozbor et al., 1983, The productrion of monoclonal antibodies from human lymphocytes. Immunology Today 4, 72-79.

Kurtzberg et al., 1996, New Eng J Med 335:157-166.

Larsson et al., 2002, Angiogenesis 5,107-110.

Lowry et al. 1980, Isolation of transforming DNA: cloning the hamster aprt gene. Cell. 22(3):817-23.

Ma et al., 1999, Tissue Engineering 5:91-102.

Melchner, et al., 1985, Human placental conditioned medium reverses apparent commitment to differentiation of human promyelocytic leukemia cells (HL60). Blood. 66(6):1469-72.

Minguel et al., 2001, Exp Biol Med 226:507-520.

Moore et al., 1997, "A simple perfusion technique for isolation of maternal intervillous blood mononuclear cells from human placentae," J. Immunol. Methods 209(1):93-104.

Muhlemann et al., 1995, Placenta 16:367-373.

Mulligan and Berg, 1981 Selection for animal cells that express the *Escherichia coli* gene coding for xanthine-guanine phosphoribosyltransferase Proc Natl Acad Sci U S A. 78(4):2072-6.

Myllynen, In Search of Models for Hepatic and Placental Pharmacokinetics, dissertation, University of Oulu (2003).

Nadkarni et al. 1984, Effect of retinoic acid on bone-marrow committed stem cells (CFU-c) from chronic myeloid leukemia patients. Tumori. 70(6):503-5.

O'Hare et al. 1981, Transformation of mouse fibroblasts to methotrexate resistance by a recombinant plasmid expressing a prokaryotic dihydrofolate reductase. Proc Natl Acad Sci U S A. 78(3):1527-31.

Ordi et al., 1998, Am J Surg Pathol 8:1006-1011.

Papaioannou et al., Stem Cell Handbook 2004, 19-31.

Placenta, Encyclopediaa Britanica, 2003.

Ray et al., 1997, CYP26, a novel mammalian cytochrome P450, in induced by retinoic acid and defines a new family.J Biol Chem. Jul. 25, 1997;272(30):18702-8.

Sakabe et al., "Functional Differences Between Subpopulations of Mobilized Peripheral Blood-Derived CD34 + Cells Expressing Different Levels of HLA-DR, CD33, CD38 and c-kit Antigens," *Stem Cells* 15(11):73-81 (1997).

Santerre et al., 1984, Expression of prokaryotic genes for hygromycin B and G418 resistance as dominant-selection markers in mouse L cells. Gene. 30(1-3):147-56.

Smithies et al. 1985, Insertion of DNA sequences into the human chromosomal beta-globin locus by homologous recombination. Nature. 317(6034):230-4.

Srour, 1999, Ex vivo expansion of hematopoietic stem and progenitor cells. Are we there yet? The Journal of Hematotherapy 8:93-102.

Szybalska and Szybalska, 1962, Genetics of human cell lines IV: DNA-mediated heritable transformation of a biochemical trait. PNAS 48: 2026-2034.

Thomas and Capecchi, 1987, Site-directed mutagenesis by gene targeting in mouse embryo-derived stem cells. Cell. 51(3):503-12.

Totipotent stem cells, Stem Cells Information Center On-line, 2004.

Totipotent stem cells, Medline Mesh Database, 2004.

Tremblay et al., 2001, Diethylstilbestrol regulates trophoblast stem cell differentiation as a ligand of orphan nuclear receptor ERR beta. Genes Dev. 15(7):833-8.

Turner et al., 1992, "A modified harvest technique for cord blood hematopoietic stem cells," Bone Marrow Transplantation 10:89-91.

Uchimura et al. 1998, Human N-acetylglucosamine-6-O-sulfotransferase involved in the biosynthesis of 6-sulfo sialyl Lewis X: molecular cloning, chromosomal mapping, and expression in various organs and tumor cells. J Biochem (Tokyo). 124(3):670-8.

Van Bekkum, "The Pluripotent Hemopoietic Stem Cell: Its Identification and Applications," *Verh. Dtsch. Ges. Pathol.* 74:19-24 (1990).

Vilmer et al., "HLA-Mismatched Cord Blood Transplantation: Immunological Studies," Blood Cells 20(2-3):242-244 (1994).

Wigler et al. 1997, Transfer of purified herpes virus thymidine kinase gene to cultured mouse cells. Cell. 11(1):223-32.

Yan et al., 2001, Retinoic acid promotes differentiation of trophoblast stem cells to a giant cell fate. Dev Biol. 235(2):422-32.

Ye et al., 2001, "Recovery of placental-derived adherent cells with mesenchymal stem cell characteristics," Blood 98(11/1):147b Abstract No. 4260.

Chen et al., "Intravenous administration of human umbilical cord blood reduces behavioral deficits after stroke in rats," STROKE 32(11):2682-2688 (2001).

Abkowitz, "Can Human Hematopoietic Stem Cells Become Skin, Gut, or Liver Cells?" N. Engl. J. Med. 346(10):770-2 (2002).

Chin et al., "Enhanced Interferon Production and Lymphokine-Activated Cytotoxicity of Human Placental Cells," *Cellular Immunology* 113:1-9 (1988).

De Coppi et al., "Human fetal stem cell isolation from amniotic fluid for tissue reconstruction," *J. Urology* 167(4 Supp.) 85 (Abstract 338) (2002).

Dushnik-Levinson, et al., "Embryogenesis in Vitro: Study of Differentiation of Embryonic Stem Cells." Biol. Neonate. 67(2):77-83.

Hatzopoulos, et al., "Isolation and Characterization of Endothelial Progenitor Cells from Mouse Embryos." Development. 125(8): 1457-68 (1998).

Himori, et al. Chemotherapeutic Susceptibility of Human Bone Marrow Progenitor Cells and Human Myelogenous Leukemia Cells (HL-60) in Co-Culture: Preliminary Report. Int. J. Cell Cloning, 2(4):254-62 (1984).

Hirashima, et al., "Maturation of Embryonic Stem Cells into Endothelial Cells in an In Vitro model of Vasculogenesis." Blood. 93(4):1253-63 (1999).

Korbling, et al., "Hepatocytes and Epithelial Cells of Donor Origin in Recipients of Peripheral-Blood Stem Cells." N. Engl. J. Med. 346(10):738-46 (2002).

Reyes, et al., "Origin of Endothelial Progenitors in Human Postnatal Bone Marrow." J. Clin. Invest. 109(3):337-46.

Sakuragawa et al., "Expression of markers for both neuronal and glial cells in human amniotic epithelial cells," *Neuroscience Letters* 209:9-12 (1996).

Sakuragawa et al., "Human amniotic epithelial cells are promising transgene carriers for allogeneic cell transplantation into liver," J. Hum. Genet. 45:171-176 (2000).

Shamblott, et al., "Derivation of Pluripotent Stem Cells from Cultured Human Primordial Germ Cells." Proc. Nat'l. Acd. Sci. U S A. 95(23):13726-31 (1998).

Slager, "Transforming Growth Factor-Beta in the Early Mouse Embryo: Implications for the Regulation of Muscle Formation and Implantation." Dev. Genet. 14(3):212-24 (1993).

Thomson, et al., "Embryonic Stem Cell Lines Derived from Human Blastocysts." Science 282(5391):1145-47 (1998).

Viacord, "Unbilical Cord Blood Can Save Lives." Informational Brochure, Boston: ViaCell CENTR-BR R1 (Oct. 2001).

Abkowitz, 2002, Can human hematopoietic stem cells become skin, gut, or liver cells? N Engl J Med. 346(10):770-2.

Dushnik-Levinson et al. 1995, Embryogenesis in vitro: study of differentiation of embryonic stem cells. Biol Neonate. 67(2):77-83.

Hatzopoulos et al. 1998, Isolation and characterization of endothelial progenitor cells from mouse embryos. Development. 125(8):1457-68.

Himori, et al . 1984, Chemotherapeutic susceptibility of human bone marrow progenitor cells and human myelogenous leukemia cells (HL-60) in co-culture: preliminary report. Int J Cell Cloning. 2(4):254-62.

Hirashima et al. 1999, Maturation of embryonic stem cells into endothelial cells in an in vitro model of vasculogenesis. Blood. 93(4):1253-63.

Korbling et al., 2002, Hepatocytes and epithelial cells of donor origin in recipients of peripheral-blood stem cells. N Engl J Med. 346(10):738-46.

Reyes et al. 2002, Origin of endothelial progenitors in human postnatal bone marrow. J Clin Invest. 109(3):337-46.

Shamblott, et al., 1998, Derivation of pluripotent stem cells from cultured human primordial germ cells. Proc Natl Acad U S A. 95(23):13726-31.

Slager 1993, Transforming growth factor-beta in the early mouse embryo: implications for the regulation of muscle formation and implantation. Dev Genet. 14(3):212-24.

Thomson et al., 1998, Embryonic stem cell lines derived from human blastocysts. Science. 282 (5391): 1145-7.

Viacord, 2001, Umbilical cord blood can save lives (Informational brochure), Boston: ViaCell CENTR-BRO R1 Oct. 2001.

Wang et al. "Enhanced Recovery of Hematopoietic Progenitor and Stem Cells from Cultivated, Postpartum Human Placenta," Blood 68:183c, Abstract 769 (2001).

* cited by examiner

EMBRYONIC-LIKE STEM CELLS DERIVED FROM POST-PARTUM MAMMALIAN PLACENTA, AND USES AND METHODS OF TREATMENT USING SAID CELLS

This application is a continuation-in-part of application Ser. No. 10/076,180, filed Feb. 13, 2002 now abandoned, which is hereby incorporated by reference herein. The present application also claims priority to U.S. provisional application No. 60/437,292, filed Dec. 31, 2002, which is hereby incorporated by reference herein.

1. INTRODUCTION

The present invention relates to the use of embryonic-like stem cells that originate from a post-partum placenta with conventional cord blood compositions or other stem or progenitor cells. The embryonic-like stem cells can be used alone or in a mixture with other stem cell populations. In accordance with the present invention, the embryonic-like stem cells may be mixed with other stem cell populations, including but not limited to, umbilical cord blood, fetal and neonatal hematopoietic stem cells and progenitor cells, human stem cells and progenitor cells derived from bone marrow. The embryonic-like stem cells and the mixed populations of embryonic-like stem cells and stem cells have a multitude of uses and applications, including but not limited to, therapeutic uses for transplantation, diagnostic and research uses. The embryonic-like stem cells and the mixed populations are also useful in the treatment of diseases or disorders, including vascular disease, neurological diseases or disorders, autoimmune diseases or disorders, diseases or disorders involving inflammation, and cancer or the disorders associated therewith. In particular, the embryonic-like stem cells or mixtures including them are administered in high doses and without HLA typing.

2. BACKGROUND OF THE INVENTION

There is considerable interest in the identification, isolation and generation of human stem cells. Human stem cells are totipotential or pluripotential precursor cells capable of generating a variety of mature human cell lineages. This ability serves as the basis for the cellular differentiation and specialization necessary for organ and tissue development.

Recent success at transplanting such stem cells have provided new clinical tools to reconstitute and/or supplement bone marrow after myeloablation due to disease, exposure to toxic chemical and/or radiation. Further evidence exists that demonstrates that stem cells can be employed to repopulate many, if not all, tissues and restore physiologic and anatomic functionality. The application of stem cells in tissue engineering, gene therapy delivery and cell therapeutics is also advancing rapidly.

Many different types of mammalian stem cells have been characterized. For example, embryonic stem cells, embryonic germ cells, adult stem cells or other committed stem cells or progenitor cells are known. Certain stem cells have not only been isolated and characterized but have also been cultured under conditions to allow differentiation to a limited extent. A basic problem remains, however, in that obtaining sufficient quantities and populations of human stem cells which are capable of differentiating into all cell types is near impossible. Stem cells are in critically short supply. These are important for the treatment of a wide variety of disorders, including malignancies, inborn errors of metabolism, hemoglobinopathies, and immunodeficiencies. It would be highly advantageous to have a source of more embryonic stem cells.

Obtaining sufficient numbers of human stem cells has been problematic for several reasons. First, isolation of normally occurring populations of stem cells in adult tissues has been technically difficult and costly due, in part, to very limited quantity found in blood or tissue. Secondly, procurement of these cells from embryos or fetal tissue, including abortuses, has raised religious and ethical concerns. The widely held belief that the human embryo and fetus constitute independent life has prompted governmental restrictions on the use of such sources for all purposes, including medical research. Alternative sources that do not require the use of cells procured from embryonic or fetal tissue are therefore essential for further progress in the use of stem cells clinically. There are, however, few viable alternative sources of stem cells, particularly human stem cells, and thus supply is limited. Furthermore, harvesting of stem cells from alternative sources in adequate amounts for therapeutic and research purposes is generally laborious, involving, e.g., harvesting of cells or tissues from a donor subject or patient, culturing and/or propagation of cells in vitro, dissection, etc.

For example, Caplan et al. (U.S. Pat. No. 5,486,359 entitled "Human mesenchymal stem cells," issued Jan. 23, 1996), discloses human mesenchymal stem cell (HMSC) compositions derived from the bone marrow that serve as the progenitors for mesenchymal cell lineages. Caplan et al. discloses that hMSCs are identified by specific cell surface markers that are identified with monoclonal antibodies. Homogeneous hMSC compositions are obtained by positive selection of adherent marrow or periosteal cells that are free of markers associated with either hematopoietic cell or differentiated mesenchymal cells. These isolated mesenchymal cell populations display epitopic characteristics associated with mesenchymal stem cells, have the ability to regenerate in culture without differentiating, and have the ability to differentiate into specific mesenchymal lineages when either induced in vitro or placed in vivo at the site of damaged tissue. The drawback of such methods, however, is that they require harvesting of marrow or periosteal cells from a donor, from which the MSCs must be subsequently isolated.

Hu et al. (WO 00/73421 entitled "Methods of isolation, cryopreservation, and therapeutic use of human amniotic epithelial cells," published Dec. 7, 2000) discloses human amniotic epithelial cells derived from placenta at delivery that are isolated, cultured, cryopreserved for future use, or induced to differentiate. According to Hu et al. a placenta is harvested immediately after delivery and the amniotic membrane separated from the chorion, e.g., by dissection. Amniotic epithelial cells are isolated from the amniotic membrane according to standard cell isolation techniques. The disclosed cells can be cultured in various media, expanded in culture, cryopreserved, or induced to differentiate. Hu et al. discloses that amniotic epithelial cells are multipotential (and possibly pluripotential), and can differentiate into epithelial tissues such as corneal surface epithelium or vaginal epithelium. The drawback of such methods, however, is that they are labor-intensive and the yield of stem cells is very low. For example, to obtain sufficient numbers of stem cells for typical therapeutic or research purposes, amniotic epithelial cells must be first isolated from the amnion by dissection and cell separation techniques, then cultured and expanded in vitro.

Umbilical cord blood ("cord blood") is a known alternative source of hematopoietic progenitor stem cells. Stem cells from cord blood are routinely cryopreserved for use in hematopoietic reconstitution, a widely used therapeutic procedure used in bone marrow and other related transplantations (see e.g., Boyse et al., U.S. Pat. No. 5,004,681, "Preservation of Fetal and Neonatal Hematopoietin Stem and Progenitor Cells of the Blood", Boyse et al., U.S. Pat. No. 5,192,553, entitled "Isolation and preservation of fetal and neonatal hematopoietic stem and progenitor cells of the blood and methods of therapeutic use", issued Mar. 9, 1993). Conventional techniques for the collection of cord blood are based on the use of a needle or cannula, which is used with the aid of gravity to drain cord blood from (i.e., exsanguinate) the placenta (Boyse et al., U.S. Pat. No. 5,192,553, issued Mar. 9, 1993; Boyse et al., U.S. Pat. No. 5,004,681, issued Apr. 2, 1991; Anderson, U.S. Pat. No. 5,372,581, entitled Method and apparatus for placental blood collection, issued Dec. 13, 1994; Hessel et al., U.S. Pat. No. 5,415,665, entitled Umbilical cord clamping, cutting, and blood collecting device and method, issued May 16, 1995). The needle or cannula is usually placed in the umbilical vein and the placenta is gently massaged to aid in draining cord blood from the placenta. Thereafter, however, the drained placenta has been regarded as having no further use and has typically been discarded. A major limitation of stem cell procurement from cord blood, moreover, has been the frequently inadequate volume of cord blood obtained, resulting in insufficient cell numbers to effectively reconstitute bone marrow after transplantation.

Naughton et al. (U.S. Pat. No. 5,962,325 entitled "Three-dimensional stromal tissue cultures" issued Oct. 5, 1999) discloses that fetal cells, including fibroblast-like cells and chondrocyte-progenitors, may be obtained from umbilical cord or placenta tissue or umbilical cord blood.

Kraus et al. (U.S. Pat. No. 6,338,942, entitled "Selective expansion of target cell populations", issued Jan. 15, 2002) discloses that a predetermined target population of cells may be selectively expanded by introducing a starting sample of cells from cord blood or peripheral blood into a growth medium, causing cells of the target cell population to divide, and contacting the cells in the growth medium with a selection element comprising binding molecules with specific affinity (such as a monoclonal antibody for CD34) for a predetermined population of cells (such as CD34 cells), so as to select cells of the predetermined target population from other cells in the growth medium.

Rodgers et al (U.S. Pat. No. 6,335,195 entitled "Method for promoting hematopoietic and mesenchymal cell proliferation and differentiation," issued Jan. 1, 2002) discloses methods for ex vivo culture of hematopoietic and mesenchymal stem cells and the induction of lineage-specific cell proliferation and differentiation by growth in the presence of angiotensinogen, angiotensin I (AI), AI analogues, AI fragments and analogues thereof, angiotensin II (AII), AII analogues, AII fragments or analogues thereof or AII $AT_2$ type 2 receptor agonists, either alone or in combination with other growth factors and cytokines. The stem cells are derived from bone marrow, peripheral blood or umbilical cord blood. The drawback of such methods, however, is that such ex vivo methods for inducing proliferation and differentiation of stem cells are time-consuming, as discussed above, and also result in low yields of stem cells.

Because of restrictions on the collection and use of stem cells, and the inadequate numbers of cells typically collected from cord blood, stem cells are in critically short supply. Stem cells have the potential to be used in the treatment of a wide variety of disorders, including malignancies, inborn errors of metabolism, hemoglobinopathies, and immunodeficiencies. There is a critical need for a readily accessible source of large numbers of human stem cells for a variety of therapeutic and other medically related purposes. The present invention addresses that need and others.

Additionally, there remains a need for the treatment of neurological conditions such as amylotrophic lateral sclerosis (ALS). Although recent studies using irradiated mouse models of familial ALS, a less-common form of ALS, have suggested that cord blood may be useful in the treatment of this disease, the source issue discussed above makes this option less than ideal. See Ende et al., *Life Sci.* 67:53059 (2000). Thus, there remains a need for stem or progenitor cell populations that can be used to treat diseases, particularly larger amounts of these populations when diseases such as ALS are being treated.

3. SUMMARY OF THE INVENTION

The present invention relates to cord blood compositions or stem or progenitor cells therefrom in which said compositions are supplemented with or contacted with embryonic-like stem cells that originate from a post-partum placenta. The embryonic-like stem cells which are the subject of other applications can be used herein as a composition or a mixture with other stem or progenitor cell populations. In accordance with the present invention, the embryonic-like stem cells may contacted with other stem or progenitor cell populations, including but not limited to, umbilical cord blood, fetal and neonatal hematopoietic stem cells and progenitor cells, human stem cells and progenitor cells derived from bone marrow. The embryonic-like stem cells and the mixed populations of embryonic-like stem cells and stem or progenitor cells have a multitude of uses and applications, including but not limited to, therapeutic uses for transplantation and treatment and prevention of disease, and diagnostic and research uses.

In accordance with the present invention, populations of stem cells are mixed with populations of embryonic-like stem cells in order to supplement, augment or enhance the concentrations of pluripotent and multipotent stem cells in the stem cell populations. for example, in one embodiment, umbilical cord blood, or stem or progenitor cells therefrom, is augmented or contacted with the embryonic-like stem cells of the invention prior to administration to the patient. It is recognized that the embryonic-like stem cells may also be administered simultaneously or sequentially with the umbilical cord blood, or cells therefrom, However, contacting the cells of each before administration is preferred.

The embryonic-like stem cells of the invention may be characterized by the presence of the following cell surface markers: CD10, CD29, CD44, CD54, CD90, SH2, SH3, SH4, OCT-4 and ABC-p, and the absence of the following cell surface markers: CD34, CD38, CD45, SSEA3 and SSEA4. In a preferred embodiment, such embryonic-like stem cells may be characterized by the presence of cell surface markers OCT-4 and APC-p. Embryonic-like stem cells originating from placenta have characteristics of embryonic stem cells but are not derived from the embryo. In other words, the invention encompasses mixtures of cord blood and embryonic-like stem cells isolated from a placenta that are OCT-4+ and/or ABC-p+. Such embryonic-like stem cells are as versatile (e.g., pluripotent) as human embryonic stem cells.

In accordance with the present invention, populations of stem cells are mixed with embryonic-like stem cells that are pluripotent or multipotent. Such embryonic-like stem cells can be isolated from the perfused placenta at different time points e.g., CD34+/CD38+, CD34+/CD38−, and CD34−/CD38− hematopoietic cells. In one embodiment, such cells may be used to supplement populations of hematopoietic stem cells, such as those found in umbilical cord blood, according to the methods of the invention.

The invention also provides a composition in which a mixture of stem cells with embryonic-like stem cells is contained within one bag or container. In a preferred embodiment, the composition is a pharmaceutically acceptable unit dose composition. In another embodiment, the invention provides a composition in which a population of stem cells and a population of embryonic-like stem cells are contained within two separate bags or containers. In certain embodiments, such a "two bag" kit may be mixed prior, in particular immediately prior to, or at the time of administration to a patient in need thereof. In other embodiments, the contents of each bag may be administered separately to a patient, wherein the mixing of the two cell populations occurs in vivo. In other embodiments, the container is sealed, air tight, and sterile.

The present invention relates to populations of stem cells are mixed with embryonic-like stem cells. In accordance with the present invention, stems cells that may be mixed with embryonic-like stem cells include, but are not limited to, umbilical cord blood, fetal and neonatal hematopoietic stem cells and progenitor cells, human stem cells and progenitor cells derived from bone marrow. In a preferred embodiment of the present invention, the embryonic-like stem cells of the invention are mixed with umbilical cord blood.

The present invention also provides methods of treating a patient in need thereof by administration of a population of stem cells supplemented with embryonic-like stem cells. In one embodiment, the supplementation of the population of cord blood cells with embryonic-like stem cells occurs by mixing the stem cells and embryonic-like stem cells prior to administration of the combined or "spiked" population to the patient. In another embodiment, the supplementation of the population of stem cells with embryonic-like stem cells occurs upon administration of the supplemented population to the patient, e.g., by simultaneous administration of the cord blood cells and the embryonic-like stem cells. In another embodiment, the supplementation of the population of stem cells with embryonic-like stem cells occurs after administration of the cord blood cells to the patient, e.g., by administering the embryonic-stem cells separately from, and before or after, administration of the stem cells.

According to the invention, populations of stem cells, e.g., umbilical cord blood, supplemented with embryonic-like stem cells from the placenta have a multitude of uses, including prophylactic, therapeutic and diagnostic uses. The supplemented populations of stem cells can be used for transplantation and/or to treat or prevent disease. In one embodiment of the invention, the supplemented populations of cells are used to renovate and repopulate tissues and organs, thereby replacing or repairing diseased tissues, organs or portions thereof. In another embodiment, the supplemented populations of stem cells can be used as a diagnostic to screen for genetic disorders or a predisposition for a particular disease or disorder.

In another embodiment, the invention provides a method for isolating other embryonic-like and/or multipotent or pluripotent stem cells from an extract or perfusate of a exsanguinated placenta and using them to supplement populations of cord blood cells according to the methods of the invention.

The present invention also provides pharmaceutical compositions that comprise populations of stem cells, e.g., umbilical cord blood cells, that have been supplemented with one or more populations of embryonic-like stem cells of the invention.

The present invention provides an isolated homogenous population of human placental stem cells that has the potential to differentiate into all cell types. In another embodiment, the population of human placental stem cells has the potential to differentiate into one cell type. In yet another embodiment, the population of human placental stem cells has the potential to differentiate into several different cell types. Such cells may be used to supplement populations of stem cells, e.g., umbilical cord blood, according to the methods of the invention.

The invention also encompasses pharmaceutical compositions that comprise populations of hematopoietic stem cells supplemented with one or more populations of cells that have high concentrations (or larger populations) of homogenous hematopoietic stem cells including, but not limited to, CD34+/CD38− cells; CD34−/CD38− cells, and CD133+ cells. One or more of these cell populations can be used with, or mixed with, hematopoietic stem cells i.e., CD34+/CD38+ hematopoietic cells, obtained from umbilical cord blood or other sources, for transplantation and other uses.

The present invention also provides methods of mixing a population of stem, progenitor or cord blood cells, including banked or cryopreserved cord blood cells, with a population of embryonic-like stem cells. In one embodiment, the two populations are physically mixed. In another aspect of this embodiment, the two populations are physically mixed and then treated with a growth factor, e.g., a cytokine and/or an interleukin, to induce cell differentiation. In another aspect of this embodiment, the stem cells and/or the embryonic-like stem cells are treated with a growth factor, e.g., a cytokine and/or an interleukin, to induce cell differentiation and then physically mixed. In one embodiment, the mixed populations are treated with a growth factor to induce differentiation into a variety of cell types. In another embodiment, the mixed populations are treated with a growth factor to induce differentiation into a particular cell type. In another embodiment, the mixed populations are treated with a growth factor to prevent or suppress differentiation into a particular cell type. In certain embodiments, the culture conditions can be controlled, e.g., the mixed population of cells can be treated with a specific cocktail of cytokines or interleukins to direct or induce differentiation to a specific cell type.

In another embodiment, the invention provides a method of treating a patient in need thereof comprising administration of a plurality of umbilical cord blood cells and a plurality of embryonic-like stem cells.

In another embodiment, the invention provides a method of treating myelodysplasia which comprises administering umbilical cord blood cells (or stem cells isolated therefrom) and embryonic-like stem cells to a patient in need thereof. The invention also relates to new uses of human placental stem cells (embryonic-like stem cells). Methods of treating or preventing disease with the compositions containing embryonic-like stem cells and other stem or progenitor cells or sources thereof are also encompassed herein. Similarly, methods of dosing such compositions are encompassed. finally, it should be noted that the compositions of the invention can contain stem or progenitor cell populations from multiple donors. The invention includes the use of non-HLA matched compositions in patients as well as HLA-matched compositions. blood type matching with the patient is preferred but not required when the compositions containing both embryonic-like stem cells and stem or progenitor cells are used.

3.1. Definitions

As used herein, the term "bioreactor" refers to an ex vivo system for propagating cells, producing or expressing biological materials and growing or culturing cells tissues, organoids, viruses, proteins, polynucleotides and microorganisms.

As used herein, the terms "cord blood" and "umbilical cord blood" are interchangeable.

As used herein, the term "embryonic stem cell" refers to a cell that is derived from the inner cell mass of a blastocyst (e.g., a 4- to 5-day-old human embryo) and that is pluripotent.

As used herein, the term "embryonic-like stem cell" refers to a cell that is not derived from the inner cell mass of a blastocyst. As used herein, an "embryonic-like stem cell" may also be referred to as a "placental stem cell," preferably a human placental stem cell derived from a post-partum perfused placenta. An embryonic-like stem cell is preferably pluripotent. However, the stem cells which may be obtained from the placenta include embryonic-like stem cells, multipotent cells, and committed progenitor cells. According to the methods of the invention, embryonic-like stem cells derived from the placenta may be collected from the isolated placenta once it has been exsanguinated and perfused for a period of time sufficient to remove residual cells.

As used herein, the term "exsanguinated" or "exsanguination," when used with respect to the placenta, refers to the removal and/or draining of substantially all cord blood from the placenta. In accordance with the present invention, exsanguination of the placenta can be achieved by, for example, but not by way of limitation, draining, gravity induced efflux, massaging, squeezing, pumping, etc. In a preferred embodiment, exsanguination of the placenta may further be achieved by perfusing, rinsing or flushing the placenta with a fluid that may or may not contain agents, such as anticoagulants, to aid in the exsanguination of the placenta.

As used herein, the term to "mix" means to combine or blend into one mass or mixture; to put together into one mass so that the constituent parts are more or less homogeneous; to create or form by combining ingredients; to form by admixture, augmentation, supplementation, or commingling; or to add an ingredient or element to another ingredient or element, and vice-versa.

As used herein, the term "perfuse" or "perfusion" refers to the act of pouring or passaging a fluid over or through an organ or tissue, preferably the passage of fluid through an organ or tissue with sufficient force or pressure to remove any residual cells, e.g., non-attached cells from the organ or tissue. As used herein, the term "perfusate" refers to the fluid collected following its passage through an organ or tissue. In a preferred embodiment, the perfusate contains one or more anticoagulants.

As used herein, the term "exogenous cell" refers to a "foreign" cell, i.e., a heterologous cell (i.e., a "non-self" cell derived from a source other than the placental donor) or autologous cell (i.e., a "self" cell derived from the placental donor) that is-derived from an organ or tissue other than the placenta.

As used herein, the term "organoid" refers to an aggregation of one or more cell types assembled in superficial appearance or in actual structure as any organ or gland of a mammalian body, preferably the human body.

As used herein, the term "multipotent cell" refers to a cell that has the capacity to grow into any of subset of the mammalian body's approximately 260 cell types. Unlike a pluripotent cell, a multipotent cell does not have the capacity to form all of the cell types.

As used herein, the term "pluripotent cell" refers to a cell that has complete differentiation versatility, i.e., the capacity to grow into any of the mammalian body's approximately 260 cell types. A pluripotent cell can be self-renewing, and can remain dormant or quiescent within a tissue. Unlike a totipotent cell (e.g., a fertilized, diploid egg cell), an embryonic stem cell cannot usually form a new blastocyst.

As used herein, the term "progenitor cell" refers to a cell that is committed to differentiate into a specific type of cell or to form a specific type of tissue.

As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells. The "stem cell" used herein includes "progenitor cells" unless otherwise noted.

As used herein, the term "totipotent cell" refers to a cell that is able to form a complete embryo (e.g., a blastocyst).

4. DETAILED DESCRIPTION OF THE INVENTION

The present invention is based in part on the unexpected discovery that embryonic-like stem cells produced by the exsanguinated, perfused and/or cultured placenta are pluripotent stem cells that can be readily differentiated into any desired cell type. These embryonic-like stem cells can be used to supplement, augment or enhance populations of stem cells, including, but not limited to umbilical cord blood, fetal and neonatal hematopoietic stem cells and progenitor cells, human stem cells and progenitor cells derived from bone marrow. In accordance with the present invention, populations of stem cells are mixed with populations of embryonic-like stem cells in order to supplement, augment or enhance the concentrations of pluripotent and multipotent stem cells in the stem cell populations. In accordance with the present invention, the populations of stem cells mixed with populations of embryonic-like stem cells have a multitude of uses and applications, including but not limited to, therapeutic uses for transplantation and treatment and prevention of disease, and diagnostic and research uses.

The invention also provides a composition in which a mixture of stem cells and embryonic-like stem cells is contained within one bag or container. In another embodiment, the invention provides a composition in which a population of stem cells and a population of embryonic-like stem cells are contained within two separate bags or containers. In certain embodiments, such a "two bag" composition may be mixed prior, in particular immediately prior, to or at the time of administration to a patient in need thereof. In other embodiments, the contents of each bag may be administered separately to a patient, wherein two cell populations are used adjunctively in vivo.

The present invention also provides methods of mixing a population of stem or progenitor cells or cord blood including banked or cryopreserved cord blood with a population of embryonic-like stem cells. In one embodiment, the two populations are physically mixed. In another aspect of this embodiment, the two populations are physically mixed and then treated with a growth factor, e.g., a cytokine and/or an interleukin, to induce cell differentiation. In another aspect of this embodiment, the stem cells and/or the embryonic-like stem cells are treated with a growth factor, e.g., a cytokine and/or an interleukin, to induce cell differentiation and then physically mixed.

The present invention also provides methods of mixing a population of committed cells, e.g., a population of cells committed to differentiate into neurons, muscle cells, hematopoietic, vascular cells, adipocytes, chondrocytes, osteocytes, hepatocytes, pancreatic, or cardiac cells, with a population of embryonic-like stem cells. In one embodiment, the two populations are physically mixed. In another aspect of this embodiment, the two populations are physically mixed and then treated with a growth factor, e.g., a cytokine and/or an interleukin, to induce cell differentiation. In another aspect of this embodiment, the committed cells and/or the embryonic-like stem cells are treated with a growth factor, e.g., a cytokine and/or an interleukin, to induce cell differentiation and then physically mixed.

According to the methods of the invention, embryonic-like stem cells are extracted from a drained placenta by means of a perfusion technique that utilizes either or both of the umbilical artery and the umbilical vein. The placenta is preferably drained by exsanguination and collection of residual blood (e.g., residual umbilical cord blood). The drained placenta is then processed in such a manner as to establish the ex vivo, natural bioreactor environment in which the resident embryonic-like stem cells within the parenchyma and extravascular space are recruited. The embryonic-like stem cells migrate into the drained, empty microcirculation where, according to the methods of the invention, they are collected, preferable by washing into a collecting vessel by perfusion.

As disclosed above, a number of different pluripotent or multipotent stem cells can be isolated from the perfused placenta at different time points during the perfusion, e.g., CD34+/CD38+, CD34+/CD38−, and CD34−/CD38− hematopoietic cells. In one embodiment, such cells may be used to supplement populations of stem cells, e.g., cord blood cells, according to the methods of the invention.

The present invention further provides an isolated homogenous population of human placental stem cells that has the potential to differentiate into all cell types. In another embodiment, the population of human placental stem cells has the potential to differentiate into one cell type. In yet another embodiment, the population of human placental stem cells has the potential to differentiate into several different cell types. Such cells may be used to supplement populations of stem cells, e.g., cord blood cells, according to the methods of the invention.

The present invention also provides methods of mixing a population of stem cells with a population of embryonic-like stem cells. In one embodiment, the two populations are physically mixed. In another aspect of this embodiment, the two populations are physically mixed and then treated with a growth factor, e.g., a cytokine and/or an interleukin, to induce cell differentiation. In another aspect of this embodiment, the stem cells and/or the embryonic-like stem cells are treated with a growth factor, e.g., a cytokine and/or an interleukin, to induce cell differentiation and then physically mixed. In one embodiment, the mixed populations are treated with a growth factor to induce differentiation into a variety of cell types. In another embodiment, the mixed populations are treated with a growth factor to induce differentiation into a particular cell type. In another embodiment, the mixed populations are treated with a growth factor to prevent or suppress differentiation into a particular cell type. In certain embodiments, the culture conditions can be controlled, e.g., the mixed population of cells can be treated with a specific cocktail of cytokines or interleukins to direct or induce differentiation to a specific cell type.

The present invention provides pharmaceutical compositions that comprise populations of stem cells, e.g., cord blood cells, that have been supplemented with one or more populations of embryonic-like stem cells of the invention.

The invention also encompasses pharmaceutical compositions that comprise populations of stem cells, e.g., cord blood cells, supplemented with one or more populations of cells that have high concentrations (or larger populations) of homogenous hematopoietic stem cells including, but not limited to, CD34+/CD38− cells; and CD34−/CD38− cells. One or more of these cell populations can be used with, or mixed with, cord blood hematopoictic cells, i.e., CD34+/CD38+ hematopoietic cells for transplantation and other uses.

According to the invention, populations of stem cells, e.g., umbilical cord blood, supplemented with embryonic-like stem cells from the placenta have a multitude of uses, including therapeutic and diagnostic uses. The supplemented populations of stem cells can be used for transplantation or to treat or prevent disease. In one embodiment of the invention, the supplemented populations of cells are used to renovate and repopulate tissues and organs, thereby replacing or repairing diseased tissues, organs or portions thereof. In another embodiment, the supplemented populations of stem cells can be used as a diagnostic to screen for genetic disorders or a predisposition for a particular disease or disorder.

The present invention also provides methods of treating a patient in need thereof by administration of a population of stem cells supplemented with embryonic-like stem cells. In one embodiment, the supplementation of the population of cord blood cells with embryonic-like stem cells occurs by mixing the stem cells and embryonic-like stem cells prior to administration of the supplemented population to the patient. In another embodiment, the supplementation of the population of stem cells with embryonic-like stem cells occurs upon administration of the supplemented population to the patient, e.g., by simultaneous administration of the cord blood cells and the embryonic-like stem cells. In another embodiment, the supplementation of the population of stem cells with embryonic-like stem cells occurs after administration of the cord blood cells to the patient, e.g., by administering the embryonic-stem cells separately from, and before or after, administration of the stem cells.

4.1. Methods of Isolating and Culturing Placenta

4.1.1. Pretreatment of Placenta

According to the methods of the invention, a human placenta is recovered shortly after its expulsion after birth and, in certain embodiments, the cord blood in the placenta is recovered. In certain embodiments, the placenta is subjected to a conventional cord blood recovery process. Such cord blood recovery may be obtained commercially, e.g., LifeBank Inc., Cedar Knolls, N.J., ViaCord, Cord Blood Registry and Cryocell. The cord blood can be drained shortly after expulsion of the placenta.

In other embodiments, the placenta is pretreated according to the methods disclosed in co-pending application Ser. No. 10/076,180, filed Feb. 13, 2002, which is incorporated herein by reference in its entirety.

4.1.2. Exsanguination of Placenta and Removal of Residual Cells

As disclosed in PCT publication WO 02/064755, published Aug. 22, 2002, which is incorporated herein by reference in its entirety, the placenta after birth contains quiescent cells that can be activated if the placenta is properly processed after birth. For example, after expulsion from the womb, the placenta is exsanguinated as quickly as possible to prevent or minimize apoptosis. Subsequently, as soon as possible after exsanguination the placenta is perfused to remove blood, residual cells, proteins, factors and any other materials present in the organ. Materials debris may also be removed from the placenta. Perfusion is normally continued with an appropriate perfusate for at least two to more than twenty-four hours. The placenta can therefore readily be used as a rich and abundant source of embryonic-like stem cells, which cells can be used for research, including drug discovery, treatment and prevention of diseases, in particular transplantation surgeries or therapies, and the generation of committed cells, tissues and organoids.

Further, surprisingly and unexpectedly, the human placental stem cells produced by the exsanguinated, perfused and/or cultured placenta are pluripotent stem cells that can readily be differentiated into any desired cell type.

According to the methods of the invention, stem or progenitor cells, including, but not limited to embryonic-like stem cells, may be recovered from a placenta that is exsanguinated, i.e., completely drained of the cord blood remaining after birth and/or a conventional cord blood recovery procedure. According to the methods of the invention, the methods for exsanguination of the placenta and removal of residual cells may be accomplished using any method known in the art, e.g., the methods disclosed in PCT publication WO 02/064755, published Aug. 22, 2002, which is incorporated herein by reference in its entirety.

4.1.3. Culturing Placenta

After exsanguination and a sufficient time of perfusion of the placenta, the embryonic-like stem cells are observed to migrate into the exsanguinated and perfused microcirculation of the placenta where, according to the methods of the invention, they are collected, preferably by washing into a collecting vessel by perfusion. In other embodiments, the placenta is cultured and the cells propagated are monitored, sorted and/or characterized according to the methods described in PCT publication WO 02/064755, published Aug. 22, 2002, which is incorporated herein by reference in its entirety.

4.2. Collection of Cells from the Placenta

After exsanguination and perfusion of the placenta, embryonic-like stem cells migrate into the drained, empty microcirculation of the placenta where, according to the invention, they are collected, preferably by collecting the effluent perfusate in a collecting vessel.

In preferred embodiments, cells cultured in the placenta are isolated from the effluent perfusate using techniques known by those skilled in the art, such as, for example, density gradient centrifugation, magnet cell separation, flow cytometry, or other cell separation or sorting methods well known in the art, and sorted.

In a specific embodiment, the embryonic-like stem cells are collected from the placenta and, in certain embodiments, preserved, according to the methods described in PCT publication WO 02/064755, published Aug. 22, 2002, which is incorporated herein by reference in its entirety.

4.3. Embryonic-Like Stem Cells

Embryonic-like stem cells obtained in accordance with the methods of the invention may include pluripotent cells, i.e., cells that have complete differentiation versatility, that are self-renewing, and can remain dormant or quiescent within tissue. The stem cells which may be obtained from the placenta include embryonic-like stem cells, multipotent cells, committed progenitor cells, and fibroblastoid cells.

The first collection of blood from the placenta is referred to as cord blood which contains predominantly CD34+ and CD38+ hematopoietic progenitor cells. Within the first twenty-four hours of post-partum perfusion, high concentrations of CD34+ and CD38− hematopoietic progenitor cells may be isolated from the placenta, along with high concentrations of CD34− and CD38+ hematopoietic progenitor cells. After about twenty-four hours of perfusion, high concentrations of CD34− and CD38− cells can be isolated from the placenta along with the aforementioned cells. The isolated perfused placenta of the invention provides a source of large quantities of stem cells enriched for CD34+ and CD38− stem cells and CD34− and CD38+ stem cells. The isolated placenta which has been perfused for twenty-four hours or more provides a source of large quantities of stem cells enriched for CD34− and CD38− stem cells.

In a preferred embodiment, embryonic-like stem cells obtained by the methods of the invention are viable, quiescent, pluripotent stem cells that exist within a full-term human placenta and that can be recovered following successful birth and placental expulsion, resulting in the recovery of as many as one billion nucleated cells, which yield 50-100 million multipotent and pluripotent stem cells.

The human placental stem cells provided by the placenta are surprisingly embryonic-like, for example, the presence of the following cell surface markers have been identified for these cells: SSEA3−, SSEA4−, OCT-4+ and ABC-p$^+$. Preferably, the embryonic-like stem cells of the invention are characterized by the presence of OCT-4+ and ABC-p$^+$ cell surface markers. Thus, the invention encompasses stem cells which have not been isolated or otherwise obtained from an embryonic source but which can be identified by the following markers: SSAE3−, SSAE4−, OCT-4+ and ABC-p$^+$. In one embodiment, the human placental stem cells do not express MHC Class 2 antigens.

The stem cells isolated from the placenta are homogenous, and sterile. Further, the stem cells are readily obtained in a form suitable for administration to humans, i.e., they are of pharmaceutical grade.

Preferred embryonic-like stem cells obtained by the methods of the invention may be identified by the presence of the following cell surface markers: OCT-4+ and ABC-pt. Further, the invention encompasses embryonic stem cells having the following markers: CD10+, CD38−, CD29+, CD34−, CD44+, CD45−, CD54+, CD90+, SH2+, SH3+, SH4+, SSEA3−, SSEA4−, OCT-4+, and ABC-p$^+$. Such cell surface markers are routinely determined according to methods well known in the art, e.g. by flow cytometry, followed by washing and staining with an anti-cell surface marker antibody. For example, to determine the presence of CD-34 or CD-38, cells may be washed in PBS and then double-stained with anti-CD34 phycoerythrin and anti-CD38 fluorescein isothiocyanate (Becton Dickinson, Mountain View, Calif.).

In another embodiment, cells cultured in the placenta bioreactor are identified and characterized by a colony forming unit assay, which is commonly known in the art, such as Mesen Cult™ medium (stem cell Technologies, Inc., Vancouver British Columbia)

The embryonic-like stem cells obtained by the methods of the invention may be induced to differentiate along specific cell lineages, including adipogenic, chondrogenic, osteogenic, hematopoietic, myogenic, vasogenic, neurogenic, and hepatogenic. In certain embodiments, embryonic-like stem cells obtained according to the methods of the invention are induced to differentiate for use in transplantation and ex vivo treatment protocols. In certain embodiments, embryonic-like stem cells obtained by the methods of the invention are induced to differentiate into a particular cell type and genetically engineered to provide a therapeutic gene product. In a specific embodiment, embryonic-like stem cells obtained by the methods of the invention are incubated with a compound in vitro that induces it to differentiate, followed by direct transplantation of the differentiated cells to a subject. Thus, the invention encompasses methods of differentiating the human placental stem cells using standard culturing media. Further, the invention encompasses hematopoietic cells, neuron cells, fibroblast cells, strand cells, mesenchymal cells and hepatic cells.

Embryonic-like stem cells may also be further cultured after collection from the placenta using methods well known in the art, for example, by culturing on feeder cells, such as irradiated fibroblasts, obtained from the same placenta as the embryonic-like stem cells or from other human or nonhuman sources, or in conditioned media obtained from cultures of such feeder cells, in order to obtain continued long-term cultures of embryonic-like stem cells. The embryonic-like stem cells may also be expanded, either within the placenta before collection from the placental bioreactor or in vitro after recovery from the placenta. In certain embodiments, the embryonic-like stem cells to be expanded are exposed to, or cultured in the presence of, an agent that suppresses cellular differentiation. Such agents are well-known in the art and include, but are not limited to, human Delta-1 and human Serrate-1 polypeptides (see, Sakano et al., U.S. Pat. No. 6,337,387 entitled "Differentiation-suppressive polypeptide", issued Jan. 8, 2002), leukemia inhibitory factor (LIF) and stem cell factor. Methods for the expansion of cell populations are also known in the art (see e.g., Emerson et al., U.S. Pat. No. 6,326,198 entitled "Methods and compositions for the ex vivo replication of stem cells, for the optimization of hematopoietic progenitor cell cultures, and for increasing the metabolism, GM-CSF secretion and/or IL-6 secretion of human stromal cells", issued Dec. 4, 2001; Kraus et al., U.S. Pat. No. 6,338,942, entitled "Selective expansion of target cell populations", issued Jan. 15, 2002).

The embryonic-like stem cells may be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

In certain embodiments, the differentiation of stem cells or progenitor cells that are cultivated in the exsanguinated, perfused and/or cultured placenta is modulated using an agent or pharmaceutical compositions comprising a dose and/or doses effective upon single or multiple administration, to exert an effect sufficient to inhibit, modulate and/or regulate the differentiation of a cell collected from the placenta.

Agents that can induce stem or progenitor cell differentiation are well known in the art and include, but are not limited to, $Ca^{2+}$, EGF, α-FGF, β-FGF, PDGF, keratinocyte growth factor (KGF), TGF-β, cytokines (e.g., IL-1α, IL-1β, IFN-γ, TFN), retinoic acid, transferrin, hormones (e.g., androgen, estrogen, insulin, prolactin, triiodothyronine, hydrocortisone, dexamethasone), sodium butyrate, TPA, DMSO, NMF, DMF, matrix elements (e.g., collagen, laminin, heparan sulfate, Matrigel™), or combinations thereof.

Agents that suppress cellular differentiation are also well-known in the art and include, but are not limited to, human Delta-1 and human Serrate-1 polypeptides (see, Sakano et al., U.S. Pat. No. 6,337,387 entitled "Differentiation-suppressive polypeptide", issued Jan. 8, 2002), leukemia inhibitory factor (LIF), and stem cell factor.

The agent used to modulate differentiation can be introduced into the placental bioreactor to induce differentiation of the cells being cultured in the placenta. Alternatively, the agent can be used to modulate differentiation in vitro after the cells have been collected or removed from the placenta.

Determination that a stem cell has differentiated into a particular cell type may be accomplished by methods well-known in the art, e.g., measuring changes in morphology and cell surface markers using techniques such as flow cytometry or immunocytochemistry (e.g., staining cells with tissue-specific or cell-marker specific antibodies), by examination of the morphology of cells using light or confocal microscopy, or by measuring changes in gene expression using techniques well known in the art, such as PCR and gene-expression profiling.

4.4. Supplementing Populations of Stem Cells with Embryonic-Like Stem Cells

The present invention relates to populations of stem cells are mixed with embryonic-like stem cells. In accordance with the present invention, stems cells that may be mixed with embryonic-like stem cells include, but are not limited to, umbilical cord blood, fetal and neonatal hematopoietic stem cells and progenitor cells, human stem cells and progenitor cells derived from bone marrow. In a preferred embodiment of the present invention, the embryonic-like stem cells of the invention are mixed with umbilical cord blood.

The present invention provides an isolated homogenous population of human placental stem cells (embryonic-like stem cells) which has the potential to differentiate into all cell types. Such cells may be used to supplement populations of stem cells, e.g., cord blood cells, according to the methods of the invention.

The invention also provides populations of cord blood cells that have been supplemented (i.e., mixed, combined or augmented) with populations of embryonic-like stem cells that originate from a placenta.

The supplemented populations are very versatile, in that they contain populations of cells that are pluripotent or multipotent stem cells, e.g., cells displaying a CD34+/CD38+, CD34+/CD38− or CD34−/CD38− phenotype.

In accordance with the present invention the supplemented populations of stem cells of the invention contain embryonic-like stem cells and other stem or progenitor cells at a ratio of 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or 1:100,000,000, comparing numbers of total nucleated cells in each population.

In another embodiment, the invention provides methods for supplementing, mixing, combining or augmenting stem cells, e.g., umbilical cord blood, with a composition of the invention, e.g., a population of pure embryonic-like placental stem cells or a population of cells enriched for embryonic-like placental stem cells. In one embodiment, an aliquot (or population) of embryonic-like placental stem cells is added to an aliquot of umbilical cord blood. before delivery to a patient in need thereof.

The present invention also provides methods of supplementing a population of cord blood cells with a population of embryonic-like stem cells. In one embodiment, the two populations are physically mixed. In another aspect of this embodiment, the two populations are physically mixed and then treated with a growth factor, e.g., a cytokine and/or an interleukin, to induce cell differentiation. In another aspect of this embodiment, the cord blood cells and/or the embryonic-like stem cells are treated with a growth factor, e.g., a cytokine and/or an interleukin, to induce cell differentiation and then physically mixed.

The present invention also provides methods of treating a patient in need thereof by administration of a population of cord blood cells supplemented with embryonic-like stem cells. In one embodiment, the supplementing of the population of cord blood cells with embryonic-like stem cells occurs by mixing the cord blood cells and embryonic-like stem cells prior to administration of the supplemented population to the patient. In another embodiment, supplementing the population of cord blood cells with embryonic-like stem cells occurs upon administration of the supplemented population to the patient, e.g., by simultaneous administration of the cord blood cells and the embryonic-like stem cells. In another embodiment, supplementing of the population of cord blood cells with embryonic-like stem cells occurs after administration of the cord blood cells to the patient, e.g., by administering the embryonic-stem cells separately from, and before or after, administration of the cord blood cells.

In one embodiment, the invention provides methods for supplementing cord blood cells with embryonic-like stem cells, wherein the mixture is contained within one bag. In another embodiment, the invention provides methods for supplementing cord blood cells with embryonic-like stem cells, wherein the cord blood cells and the embryonic-like stem cells are each contained in a separate bags. Such a "two bag" composition may be mixed prior to or at the time of administration to a patient in need thereof.

In another embodiment, an aliquot (or population) of embryonic-like placental stem cells are conditioned before being added to, and mixed into, an aliquot of umbilical cord blood before delivery to a patient in need thereof. For example, in one aspect of this embodiment, a population of embryonic-like placental stem cells is induced to differentiate into a particular cell lineage, e.g., a hematopoietic, neuronal, adipogenic, chondrogenic, osteogenic, hepatogenic, pancreatic, or myogenic lineage, as disclosed above in Section 4.3, by exposure to, e.g., cytokines (e.g., IL-1α, IL-1β, IFN-γ, TFN), retinoic acid, transferrin, hormones (e.g., androgen, estrogen, insulin, prolactin, triiodothyronine, hydrocortisone, dexamethasone), sodium butyrate, TPA, DMSO, NMF, DMF, matrix elements (e.g., collagen, laminin, heparan sulfate, Matrigel™), or combinations thereof, before being added to, and mixed into, an aliquot of umbilical cord blood.

In another aspect of this embodiment, a population of embryonic-like placental stem cells is conditioned by being exposed to an agent that suppresses differentiation, e.g., human Delta-1 and human Serrate-1 polypeptides, or combinations thereof, before being added to, and mixed into, an aliquot of umbilical cord blood.

In another embodiment, an aliquot (or population) of non-conditioned embryonic-like placental stem cells and an aliquot of umbilical cord blood are mixed, and the mixed population of cells is conditioned before being delivery to a patient in need thereof. In specific embodiments, the mixed population of embryonic-like placental stem cells and umbilical cord blood cells are conditioned with an agent that induces or suppresses cell differentiation as disclosed above.

In a specific embodiment, a population of embryonic-like stem cells of the invention is added to, or mixed into, a population of umbilical cord blood cells prior to administration to a patient in need thereof. In another specific embodiment, a population of embryonic-like stem cells of the invention is added to, or mixed into, a population of umbilical cord blood cells during, or simultaneous with, administration to a patient in need thereof. In another specific embodiment, a population of embryonic-like stem cells of the invention and a population of umbilical cord blood cells are administered sequentially to a patient in need thereof. In one embodiment, the population of embryonic-like stem cells is administered first and the population of umbilical cord blood cells is administered second. In another embodiment, the population of umbilical cord blood cells is administered first and the population of embryonic-like placental stem cells is administered second.

The populations of cord blood cells spiked with embryonic-like stem cells may be cultured, induced to propagate, and/or induced to differentiate under a variety of conditions, including but not limited to treating the spiked populations by introduction of nutrients, hormones, vitamins, growth factors, or any combination thereof, into the culture medium. Serum and other growth factors may be added to the culture medium. Growth factors are usually proteins and include, but are not limited to: cytokines, lymphokines, interferons, colony stimulating factors (CSF's), interferons, chemokines, and interleukins. Other growth factors that may be used include recombinant human hematopoictic growth factors including ligands, stem cell factors, thrombopoeitin (Tpo), granulocyte colony-stimulating factor (G-CSF), leukemia inhibitory factor, basic fibroblast growth factor, placenta derived growth factor and epidermal growth factor. In one embodiment, the supplemented populations are treated with a growth factor to induce differentiation into a variety of cell types. In another embodiment, the spiked populations are treated with a growth factor to induce differentiation into a particular cell type. In another embodiment, the supplemented populations are treated with a growth factor to prevent or suppress differentiation into a particular cell type.

In certain embodiments of the invention, the methods of supplementing a population of cord blood comprise (a) induction of differentiation of embryonic-like stem cells, (b) mixing the embryonic-like stem cells with a population of cord blood cells and (c) administration of the mixture to a patient in need thereof.

In other embodiments of the invention, the methods of supplementing a population of cord blood comprise (a) mixing the embryonic-like stem cells with a population of cord blood cells; (b) induction of differentiation of the mixture of the spiked population of cord blood cells and embryonic-like stem cells and (c) administration of the mixture to a patient in need thereof.

In other embodiments of the invention, the methods of supplementing a population of cord blood comprise (a) administration of a mixture of cord blood cells supplemented with embryonic-like stem cells to a patient in need thereof and (b) induction of differentiation of the mixture and (c) administration of the mixture to a patient in need thereof.

In certain embodiments, stem or progenitor cells are induced to differentiate into a particular cell type, by exposure to a growth factor, according to methods well known in the art. In specific embodiments, the growth factor is: GM-CSF, IL-4, Flt3L, CD40L, IFN-alpha, TNF-alpha, IFN-gamma, IL-2, IL-6, retinoic acid, basic fibroblast growth factor, TGF-beta-1, TGF-beta-3, hepatocyte growth factor, epidermal growth factor, cardiotropin-1, angiotensinogen, angiotensin I (AI), angiotensin II (AII), AII $AT_2$ type 2 receptor agonists, or analogs or fragments thereof.

In one embodiment, stem or progenitor cells are induced to differentiate into neurons, according to methods well known in the art, e.g., by exposure to β-mercaptoethanol or to DMSO/butylated hydroxyanisole, according to the methods disclosed in Section 5.4.1.

In another embodiment, stem or progenitor cells are induced to differentiate into adipocytes, according to methods well known in the art, e.g., by exposure to dexamethasone, indomethacin, insulin and IBMX, according to the methods disclosed in Section 5.4.2.

In another embodiment, stem or progenitor cells are induced to differentiate into chondrocytes, according to methods well known in the art, e.g., by exposure to TGF-beta-3, according to the methods disclosed in Section 5.4.3.

In another embodiment, stem or progenitor cells are induced to differentiate into osteocytes, according to methods well known in the art, e.g., by exposure to dexamethasone, ascorbic acid-2-phosphate and beta-glycerophosphate, according to the methods disclosed in Section 5.4.4.

In another embodiment, stem or progenitor cells are induced to differentiate into hepatocytes, according to methods well known in the art, e.g., by exposure to IL-6+/–IL-15, according to the methods disclosed in Section 5.4.5.

In another embodiment, stem or progenitor cells are induced to differentiate into pancreatic cells, according to methods well known in the art, e.g., by exposure to basic fibroblast growth factor, and transforming growth factor beta-1, according to the methods disclosed in Section 5.4.6.

In another embodiment, stem or progenitor cells are induced to differentiate into cardiac cells, according to methods well known in the art, e.g., by exposure to retinoic acid, basic fibroblast growth factor, TGF-beta-1 and epidermal growth factor, by exposure to cardiotropin-1 or by exposure to human myocardium extract, according to the methods disclosed in Section 5.4.7.

In another embodiment, the embryonic-like stem cells are stimulated to produce bioactive molecules, such as immunoglobulins, hormones, enzymes.

In another embodiment, the embryonic-like stem cells are stimulated to proliferate, for example, by administration of erythropoietin, cytokines, lymphokines, interferons, colony stimulating factors (CSF's), interferons, chemokines, interleukins, recombinant human hematopoietic growth factors including ligands, stem cell factors, thrombopoeitin (Tpo), interleukins, and granulocyte colony-stimulating factor (G-CSF) or other growth factors.

In another embodiment, the embryonic-like stem cells are genetically engineered either prior to, or after collection from, the placenta, using, for example, a viral vector such as an adenoviral or retroviral vector, or by using mechanical means such as liposomal or chemical mediated uptake of the DNA.

A vector containing a transgene can be introduced into a cell of interest by methods well known in the art, e.g., transfection, transformation, transduction, electroporation, infection, microinjection, cell fusion, DEAE dextran, calcium phosphate precipitation, liposomes, LIPOFECTIN™, lysosome fusion, synthetic cationic lipids, use of a gene gun or a DNA vector transporter, such that the transgene is transmitted to daughter cells, e.g., the daughter embryonic-like stem cells or progenitor cells produced by the division of an embryonic-like stem cell. For various techniques for transformation or transfection of mammalian cells, see Keown et al., 1990, Methods Enzymol. 185: 527-37; Sambrook et al., 2001, Molecular Cloning, A Laboratory Manual, Third Edition, Cold Spring Harbor Laboratory Press, N.Y.

Preferably, the transgene is introduced using any technique, so long as it is not destructive to the cell's nuclear membrane or other existing cellular or genetic structures. In certain embodiments, the transgene is inserted into the nucleic genetic material by microinjection. Microinjection of cells and cellular structures is commonly known and practiced in the art.

For stable transfection of cultured mammalian cells, such as the embryonic-like stem cells, only a small fraction of cells may integrate the foreign DNA into their genome. The efficiency of integration depends upon the vector and transfection technique used. In order to identify and select integrants, a gene that encodes a selectable marker (e.g., for resistance to antibiotics) is generally introduced into the host embryonic-like stem cell along with the gene sequence of interest. Preferred selectable markers include those that confer resistance to drugs, such as G418, hygromycin and methotrexate. Cells stably transfected with the introduced nucleic acid can be identified by drug selection (e.g., cells that have incorporated the selectable marker gene will survive, while the other cells die). Such methods are particularly useful in methods involving homologous recombination in mammalian cells (e.g., in embryonic-like stem cells) prior to introduction or transplantation of the recombinant cells into a subject or patient.

A number of selection systems may be used to select transformed host embryonic-like cells. In particular, the vector may contain certain detectable or selectable markers. Other methods of selection include but are not limited to selecting for another marker such as: the herpes simplex virus thymidine kinase (Wigler et al., 1977, Cell 11: 223), hypoxanthine-guanine phosphoribosyltransferase (Szybalska and Szybalski, 1962, Proc. Natl. Acad. Sci. USA 48: 2026), and adenine phosphoribosyltransferase (Lowy et al., 1980, Cell 22: 817) genes can be employed in tk-, hgprt- or aprt-cells, respectively. Also, antimetabolite resistance can be used as the basis of selection for the following genes: dhfr, which confers resistance to methotrexate (Wigler et al., 1980, Proc. Natl. Acad. Sci. USA 77: 3567; O'Hare et al., 1981, Proc. Natl. Acad. Sci. USA 78: 1527); gpt, which confers resistance to mycophenolic acid (Mulligan and Berg, 1981, Proc. Natl. Acad. Sci. USA 78: 2072); neo, which confers resistance to the aminoglycoside G-418 (Colberre-Garapin et al., 1981, J. Mol. Biol. 150: 1); and hygro, which confers resistance to hygromycin (Santerre et al., 1984, Gene 30: 147).

The transgene may integrate into the genome of the cell of interest, preferably by random integration. In other embodiments the transgene may integrate by a directed method, e.g., by directed homologous recombination (i.e., "knock-in" or "knock-out" of a gene of interest in the genome of cell of interest), Chappel, U.S. Pat. No. 5,272,071; and PCT publication No. WO 91/06667, published May 16, 1991; U.S. Pat. No. 5,464,764; Capecchi et al., issued Nov. 7, 1995; U.S. Pat. No. 5,627,059, Capecchi et al. issued, May 6, 1997; U.S. Pat. No. 5,487,992, Capecchi et al., issued Jan. 30, 1996).

Methods for generating cells having targeted gene modifications through homologous recombination are known in the art. The construct will comprise at least a portion of a gene of interest with a desired genetic modification, and will include regions of homology to the target locus, i.e., the endogenous copy of the targeted gene in the host's genome. DNA constructs for random integration, in contrast to those used for homologous recombination, need not include regions of homology to mediate recombination. Markers can be included in the targeting construct or random construct for performing positive and negative selection for insertion of the transgene.

To create a homologous recombinant cell, e.g., a homologous recombinant embryonic-like stem cell, endogenous placental cell or exogenous cell cultured in the placenta, a homologous recombination vector is prepared in which a gene of interest is flanked at its 5' and 3' ends by gene sequences that are endogenous to the genome of the targeted cell, to allow for homologous recombination to occur between the gene of interest carried by the vector and the endogenous gene in the genome of the targeted cell. The additional flanking nucleic acid sequences are of sufficient length for successful homologous recombination with the endogenous gene in the genome of the targeted cell. Typically, several kilobases of flanking DNA (both at the 5' and 3' ends) are included in the vector. Methods for constructing homologous recombination vectors and homologous recombinant animals from recombinant stem cells are commonly known in the art (see, e.g., Thomas and Capecchi, 1987, Cell 51: 503; Bradley, 1991, Curr. Opin. Bio/Technol. 2: 823-29; and PCT Publication Nos. WO 90/11354, WO 91/01140, and WO 93/04169.

In one embodiment, the genome of an exogenous cell cultured in the placenta according to the methods of the invention is a target of gene targeting via homologous recombination or via random integration.

In a specific embodiment, the methods of Bonadio et al. (U.S. Pat. No. 5,942,496, entitled Methods and compositions for multiple gene transfer into bone cells, issued Aug. 24, 1999; and PCT WO95/226 11, entitled Methods and compositions for stimulating bone cells, published Aug. 24, 1995) are used to introduce nucleic acids into a cell of interest, such as a stem cell, progenitor cell or exogenous cell cultured in the placenta, e.g., bone progenitor cells.

4.5. Uses of Embryonic-Like Stem Cells and Supplemented Populations of Stem Cells Embryonic-like stem cells may be obtained from perfused placentas according to the methods described in copending U.S. application Ser. No. 01/076,180, filed Feb. 13, 2002.

The placental stem cell (embryonic-like stem cell) may be induced to differentiate into a particular cell type, either ex vivo or in vivo. For example, pluripotent embryonic-like stem cells may be injected into a damaged organ, and for organ neogenesis and repair of injury in vivo. Such injury may be due to such conditions and disorders including, but not limited to, myocardial infarction, seizure disorder, multiple sclerosis, stroke, hypotension, cardiac arrest, ischemia, inflammation, age-related loss of cognitive function, radiation damage, cerebral palsy, neurodegenerative disease, Alzheimer's disease, Parkinson's disease, Leigh disease, AIDS dementia, memory loss, amyotrophic lateral sclerosis, ischemic renal disease, brain or spinal cord trauma, heart-lung bypass, glaucoma, retinal ischemia, or retinal trauma.

The embryonic-like stem cells isolated from the placenta, alone or in combination with stem or progenitor cell populations (i.e., the cell compositions of the invention) may be used, in specific embodiments, in autologous or heterologous enzyme replacement therapy to treat specific diseases or conditions, including, but not limited to lysosomal storage diseases, such as Tay-Sachs, Niemann-Pick, Fabry's, Gaucher's, Hunter's, and Hurler's syndromes, as well as other gangliosidoses, mucopolysaccharidoses, and glycogenoses.

In other embodiments, the embryonic-like stem cells, alone or in combination with stem or progenitor cell populations, may be used as autologous or heterologous transgene carriers in gene therapy to correct inborn errors of metabolism, adrenoleukodystrophy, cystic fibrosis, glycogen storage disease, hypothyroidism, sickle cell anemia, Pearson syndrome, Pompe's disease, phenylketonuria (PKU), porphyrias, maple syrup urine disease, homocystinuria, mucoplysaccharide nosis, chronic granulomatous disease and tyrosinemia and Tay-Sachs disease or to treat cancer, tumors or other pathological conditions.

In other embodiments, the cell compositions may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

The large numbers of embryonic-like stem cells and/or progenitor obtained using the methods of the invention would, in certain embodiments, reduce the need for large bone marrow donations. Approximately $1 \times 10^8$ to $2 \times 10^8$ bone marrow mononuclear cells per kilogram of patient weight must be infused for engraftment in a bone marrow transplantation (i.e., about 70 ml of marrow for a 70 kg donor). To obtain 70 ml requires an intensive donation and significant loss of blood in the donation process. In a specific embodiment, cells from a small bone marrow donation (e.g., 7-10 ml) could be expanded by propagation in a placental bioreactor before infusion into a recipient.

Furthermore, a small number of stem cells and progenitor cells normally circulate in the blood stream. In another embodiment, such exogenous stem cells or exogenous progenitor cells are collected by apheresis, a procedure in which blood is withdrawn, one or more components are selectively removed, and the remainder of the blood is reinfused into the donor. The exogenous cells recovered by apheresis are expanded by propagation in a placental bioreactor, thus eliminating the need for bone marrow donation entirely.

While the blood cells regenerate between chemotherapy treatments, however, the cancer has time to grow and possibly become more resistant to the chemotherapy drugs due to natural selection. Therefore, the longer chemotherapy is given and the shorter the duration between treatments, the greater the odds of successfully killing the cancer. To shorten the time between chemotherapy treatments, embryonic-like stem cells or progenitor cells collected according to the methods of the invention, alone or in combination with other stem cell or progenitor cell populations, could be introduced into the patient. Such treatment would reduce the time the patient would exhibit a low blood cell count, and would therefore permit earlier resumption of the chemotherapy treatment.

The embryonic-like stem cells, progenitor cells, foreign cells, or engineered cells obtained from a placenta according to the methods of the invention, alone or in combination with other stem cell or progenitor cell populations, can be used in the manufacture of a tissue or organ in vivo. The methods of the invention encompass using cells obtained from the placenta, e.g., embryonic-like stem cells, progenitor cells, or foreign stem or progenitor cells, to seed a matrix and to be cultured under the appropriate conditions to allow the cells to differentiate and populate the matrix. The tissues and organs obtained by the methods of the invention may be used for a variety of purposes, including research and therapeutic purposes.

The embryonic-like stem cells and the supplemented populations of stem cells of the invention can also be used for a wide variety of prophylactic or therapeutic protocols in which a tissue or organ of the body is augmented, repaired or replaced by the engraftment, transplantation or infusion of a desired cell population, such as a stem cell or progenitor cell population. The embryonic-like stem cells and the supplemented populations of stem cells of the invention can be used to replace or augment existing tissues, to introduce new or altered tissues, or to join together biological tissues or structures. The embryonic-like stem and supplemented stem cell populations of the invention can also be substituted for embryonic stem cells in therapeutic protocols described herein in which embryonic stem cells would be typically be used.

In a preferred embodiment of the invention, embryonic-like stem cells and supplemented stem cell populations may be used as autologous and allogenic, including matched and mismatched HLA type hematopoietic transplants. In accordance with the use of embryonic-like stem cells as allogenic hematopoietic transplants it may be necessary to treat the host to reduce immunological rejection of the donor cells, such as those described in U.S. Pat. No. 5,800,539, issued Sep. 1, 1998; and U.S. Pat. No. 5,806,529, issued Sep. 15, 1998, both of which are incorporated herein by reference.

For example, embryonic-like stem cells and supplemented stem cell populations of the invention can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair.

Embryonic-like stem cells and supplemented stem cell populations may be used instead of specific classes of progenitor cells (e.g., chondrocytes, hepatocytes, hematopoietic cells, pancreatic parenchymal cells, neuroblasts, muscle progenitor cells, etc.) in therapeutic or research protocols in which progenitor cells would typically be used.

Embryonic-like stem cells and supplemented stem cell populations of the invention can be used for augmentation, repair or replacement of cartilage, tendon, or ligaments. For example, in certain embodiments, prostheses (e.g., hip prostheses) are coated with replacement cartilage tissue constructs grown from embryonic-like stem cells of the invention. In other embodiments, joints (e.g., knee) are reconstructed with cartilage tissue constructs grown from embryonic-like stem cells. Cartilage tissue constructs can also be employed in major reconstructive surgery for different types of joints (for protocols, see e.g., Resnick, D., and Niwayama, G., eds., 1988, Diagnosis of Bone and Joint Disorders, 2d ed., W. B. Saunders Co.).

The embryonic-like stem cells and supplemented stem cell populations of the invention can be used to repair damage of tissues and organs resulting from trauma, metabolic disorders, or disease. In such an embodiment, a patient can be administered embryonic-like stem cells, alone or combined with other stem or progenitor cell populations, to regenerate or restore tissues or organs which have been damaged as a consequence of disease, e.g., enhance immune system following chemotherapy or radiation, repair heart tissue following myocardial infarction.

The embryonic-like stem cells and supplemented stem cell populations of the invention can be used to augment or replace bone marrow cells in bone marrow transplantation. Human autologous and allogenic bone marrow transplantation are currently used as therapies for diseases such as leukemia, lymphoma and other life-threatening disorders. The drawback of these procedures, however, is that a large amount of donor bone marrow must be removed to insure that there is enough cells for engraftment.

The embryonic-like stem cells and supplemented stem cell populations of the invention can provide stem cells and progenitor cells that would reduce the need for large bone marrow donation. It would also be, according to the methods of the invention, to obtain a small marrow donation and then expand the number of stem cells and progenitor cells culturing and expanding in the placenta before infusion or transplantation into a recipient.

The embryonic-like stem cells and supplemented stem cell populations of the invention may be used, in specific embodiments, in autologous or heterologous enzyme replacement therapy to treat specific diseases or conditions, including, but not limited to lysosomal storage diseases, such as Tay-Sachs, Niemann-Pick, Fabry's, Gaucher's, Hunter's, Hurler's syndromes, as well as other gangliosidoses, mucopolysaccharidoses, and glycogenoses.

In other embodiments, the cells may be used as autologous or heterologous transgene carriers in gene therapy to correct inborn errors of metabolism such as adrenoleukodystrophy, cystic fibrosis, glycogen storage disease, hypothyroidism, sickle cell anemia, Pearson syndrome, Pompe's disease, phenylketonuria (PKU), and Tay-Sachs disease, porphyrias, maple syrup urine disease, homocystinuria, mucopolypsaccharide nosis, chronic granulomatous disease, and tyrosinemia. or to treat cancer, tumors or other pathological or neoplastic conditions.

In other embodiments, the cells may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, scalp (hair) transplantation, or for reconstruction of other damaged or diseased organs or tissues.

The large numbers of embryonic-like stem cells and/or progenitor obtained using the methods of the invention would, in certain embodiments, reduce the need for large bone marrow donations. Approximately $1 \times 10^8$ to $2 \times 10^8$ bone marrow mononuclear cells per kilogram of patient weight must be infused for engraftment in a bone marrow transplantation (i.e., about 70 ml of marrow for a 70 kg donor). To obtain 70 ml requires an intensive donation and significant loss of blood in the donation process. In a specific embodiment, cells from a small bone marrow donation (e.g., 7-10 ml) could be expanded by propagation in a placental bioreactor before infusion into a recipient.

In another embodiment, the embryonic-like stem cells and supplemented stem cell populations of the invention can be used in a supplemental treatment in addition to chemotherapy. Most chemotherapy agents used to target and destroy cancer cells act by killing all proliferating cells, i.e., cells going through cell division. Since bone marrow is one of the most actively proliferating tissues in the body, hematopoietic stem cells are frequently damaged or destroyed by chemotherapy agents and in consequence, blood cell production is diminishes or ceases. Chemotherapy must be terminated at intervals to allow the patient's hematopoietic system to replenish the blood cell supply before resuming chemotherapy. It may take a month or more for the formerly quiescent stem cells to proliferate and increase the white blood cell count to acceptable levels so that chemotherapy may resume (when again, the bone marrow stem cells are destroyed).

While the blood cells regenerate between chemotherapy treatments, however, the cancer has time to grow and possibly become more resistant to the chemotherapy drugs due to natural selection. Therefore, the longer chemotherapy is given and the shorter the duration between treatments, the greater the odds of successfully killing the cancer. To shorten the time between chemotherapy treatments, embryonic-like stem cells or progenitor cells collected according to the methods of the invention could be introduced into the patient. Such treatment would reduce the time the patient would exhibit a low blood cell count, and would therefore permit earlier resumption of the chemotherapy treatment.

In another embodiment, the human placental stem cells can be used to treat or prevent genetic diseases such as chronic granulomatous disease.

4.6. Pharmaceutical Compositions

The present invention encompasses pharmaceutical compositions which comprise the embryonic-like stem cells and supplemented stem cell populations of the invention. The present invention encompasses pharmaceutical compositions comprising a dose and/or doses effective upon single or multiple administration, prior to or following transplantation of conditioned or unconditioned human progenitor stem cells, that are able to exert an effect sufficient to inhibit, modulate and/or regulate the differentiation of human pluripotent and multipotent progenitor stem cells of placental origin into one or more cell lineages, for example, mesodermal, adipose, chondrocytic, osteocytic, myocytic, vascular, neural, endothelial, hepatic, kidney, pancreatic, and/or hematopoietic lineage cells.

In accordance with this embodiment, the embryonic-like stem cells and supplemented stem cell populations of the invention may be formulated as an injectable (e.g., PCT WO 96/39101, incorporated herein by reference in its entirety). In an alternative embodiment, the cells and tissues of the present invention may be formulated using polymerizable or cross linking hydrogels as described in U.S. Pat. Nos. 5,709,854; 5,516,532; 5,654,381; each of which is incorporated by reference in their entirety. The embryonic-like stem cells may be administered as obtained from the placenta, or may be spiked into umbilical cord blood and administered as a mixed cell composition, or may be placed into any physiologically-acceptable buffer or fluid for administration to an individual.

The invention also encompasses pharmaceutical compositions that have high concentrations (or larger populations) of homogenous embryonic-like stem cells, wherein one or more of these cell populations can be used with, or as a mixture with, other stem or progenitor cells, for use in transplantation and other uses. Other stem or progenitor cells may include but are not limited to: adipogenic, chondrogenic, osteogenic, hematopoietic, myogenic, vasogenic, neurogenic, and hepatogenic stem cells; mesenchymal stem cells, stromal cells, endothelial cells, hepatocytes, keratinocytes, and stem or progenitor cells for a particular cell type, tissue or organ, including but not limited to neurons, myelin, muscle, blood, bone marrow, skin, heart, connective tissue, lung, kidney, liver, and pancreas (e.g., pancreatic islet cells).

In one embodiment, the invention provides pharmaceutical compositions that have high concentrations (or larger populations) of homogenous hematopoietic stem cells including but not limited to CD34+/CD38− cells; and CD34−/CD38− cells. One or more of these cell populations can be used with, or as a mixture with, other stem cells, for use in transplantation and other uses. In a specific embodiment, the pharmaceutical composition comprises embryonic-like placental stem cells of the invention and cord blood hematopoietic cells i.e., CD34+/CD38+ hematopoietic cells. One or more of these cell populations can be used with or as a mixture with cord blood hematopoietic cells i.e., CD34+/CD38+ hematopoietic cells for transplantation and other uses.

In one embodiment, the invention provides heterogeneous population of nucleated cells that comprises embryonic-like placental stem cells. In certain embodiments, a heterogeneous population of nucleated cells (rather than a pure population CD34+ cells embryonic-like placental stem cells) is preferred.

In another embodiment, the invention provides a mixed population of cells (e.g., cord blood cells and embryonic-like placental stem cells). The population of mixed cells may be frozen or unfrozen. Such a mixed population may be stored and/or used in one container, e.g., one bag or one syringe.

In another embodiment, the invention provides two or more separate or distinct populations of different cell types (e.g., cord blood cells and embryonic-like placental stem cells). Each separate population may be stored and/or used in a separate container, e.g., one bag (e.g., blood storage bag from Baxter, Becton-Dickinson, Medcep, National Hospital Products or Terumo) or one syringe, which contains a single type of cell or cell population.

In certain aspects of this embodiment, the invention provides separate containers of different cell types to be mixed before administration. Such cells may be unfrozen or frozen.

In a specific embodiment, cord blood cells are contained in one bag and embryonic-like placental stem cells are contained in a second bag. In another embodiment, the invention provides embryonic-like placental stem cells that are "conditioned" before freezing.

In another embodiment, a population of cells including, but not limited to, embryonic-like placental stem cells may be conditioned by the removal of red blood cells and/or granulocytes according to standard methods, so that a population of nucleated cells remains that is enriched for embryonic-like placental stem cells. Such an enriched population of embryonic-like placental stem cells may be used unfrozen, or frozen for later use. If the population of cells is to be frozen, a standard cryopreservative (e.g., DMSO, glycerol, Epilife™ Cell Freezing Medium (Cascade Biologics)) is added to the enriched population of cells before it is frozen.

In another embodiment, a population of cells including, but not limited to, embryonic-like placental stem cells may be conditioned by the removal of red blood cells and/or granulocytes after it has been frozen and thawed.

According to the invention, agents that induce cell differentiation may be used to condition a population of embryonic-like stem cells. In certain embodiments, an agent that induces differentiation can be added to a population of cells within a container, including, but not limited to, $Ca^{2+}$, EGF, α-FGF, β-FGF, PDGF, keratinocyte growth factor (KGF), TGF-β, cytokines (e.g., IL-1α, IL-1β, IFN-γ, TFN), retinoic acid, transferrin, hormones (e.g., androgen, estrogen, insulin, prolactin, triiodothyronine, hydrocortisone, dexamethasone), sodium butyrate, TPA, DMSO, NMF, DMF, matrix elements (e.g., collagen, laminin, heparan sulfate, Matrigel™), or combinations thereof.

In another embodiment, agents that suppress cellular differentiation can be added to a population of embryonic-like stem cells. In certain embodiments, an agent that suppresses differentiation can be added to a population of cells within a container, including, but not limited to, human Delta-1 and human Serrate-1 polypeptides (see, Sakano et al., U.S. Pat. No. 6,337,387 entitled "Differentiation-suppressive polypeptide", issued Jan. 8, 2002), leukemia inhibitory factor (LIF), stem cell factor, or combinations thereof.

In certain embodiments, one or more populations of embryonic-like stem cells are delivered to a patient in need thereof. In certain embodiments, two or more populations of fresh (never frozen) cells are delivered from a single container or single delivery system.

In another embodiment, two or more populations of frozen and thawed cells are delivered from a single container or single delivery system.

In another embodiment, each of two or more populations of fresh (never frozen) cells are transferred to, and delivered from, a single container or single delivery system. In another embodiment, each of two or more populations of frozen and thawed cells are transferred to, and delivered from, a single container or single delivery system. In another aspect of these embodiments, each population is delivered from a different IV infusion bag (e.g., from Baxter, Becton-Dickinson, Medcep, National Hospital Products or Terumo). The contents of each container (e.g., IV infusion bag) may be delivered via a separate delivery system, or each container may be "piggybacked" so that their contents are combined or mixed before delivery from a single delivery system. For example, the two or more populations of cells may be fed into and/or mixed within a common flow line (e.g., tubing), or they may be fed into and/or mixed within a common container (e.g., chamber or bag).

According to the invention, the two or more populations of cells may be combined before administration, during or at administration or delivered simultaneously.

In one embodiment, a minimum of $1.7 \times 10^7$ nucleated cells/kg is delivered to a patient in need thereof. Preferably, at least $2.5 \times 10^7$ nucleated cells/kg is delivered to a patient in need thereof.

In one embodiment, the invention provides a method of treating or preventing a disease or disorder in a subject comprising administering to a subject in which such treatment or prevention is desired a therapeutically effective amount of the embryonic-like stem cells, or supplemental cell populations, of the invention.

In another embodiment, the invention provides a method of treating or preventing a disease or disorder in a subject comprising administering to a subject in which such treatment or prevention is desired a therapeutically effective amount of the embryonic-like stem cells of the invention.

The embryonic-like stem cells of the invention are expected to have an anti-inflammatory effect when administered to an individual experiencing inflammation. In a preferred embodiment, the embryonic-like stem cells or supplemental cell populations of the invention may be used to treat any disease, condition or disorder resulting from, or associated with, inflammation. The inflammation may be present in any organ or tissue, for example, muscle; nervous system, including the brain, spinal cord and peripheral nervous system; vascular tissues, including cardiac tissue; pancreas; intestine or other organs of the digestive tract; lung; kidney; liver; reproductive organs; endothelial tissue, or endodermal tissue.

The embryonic-like stem cells or supplemented cell populations of the invention may also be used to treat autoimmune or immune system-related disorders, including those associated with inflammation. Thus, in certain embodiments, the invention provides a method of treating an individual having an autoimmune disease or condition, comprising administering to such individual a therapeutically effective amount of the cells or supplemented cell populations of the invention, wherein said disease or disorder can be, but is not limited to, diabetes, amylotrophic lateral sclerosis, myasthenia gravis, diabetic neuropathy or lupus. In related embodiments, the embryonic-like stem cells or supplemented cell populations of the invention may be used to treat immune-related disorders, such as chronic or acute allergies.

In certain embodiments, the disease or disorder includes, but is not limited to, any of the diseases or disorders disclosed herein, including, but not limited to aplastic anemia, myelodysplasia, myocardial infarction, seizure disorder, multiple sclerosis, stroke, hypotension, cardiac arrest, ischemia, inflammation, age-related loss of cognitive function, radiation damage, cerebral palsy, neurodegenerative disease, Alzheimer's disease, Parkinson's disease, Leigh disease, AIDS dementia, memory loss, amyotrophic lateral sclerosis (ALS), ischemic renal disease, brain or spinal cord trauma, heart-lung bypass, glaucoma, retinal ischemia, retinal trauma, lysosomal storage diseases, such as Tay-Sachs, Niemann-Pick, Fabry's, Gaucher's, Hunter's, and Hurler's syndromes, as well as other gangliosidoses, mucopolysaccharidoses, glycogenoses, inborn errors of metabolism, adrenoleukodystrophy, cystic fibrosis, glycogen storage disease, hypothyroidism, sickle cell anemia, Pearson syndrome, Pompe's disease, phenylketonuria (PKU), porphyrias, maple syrup urine disease, homocystinuria, mucoplysaccharide nosis, chronic granulomatous disease and tyrosinemia, Tay-Sachs disease, cancer, tumors or other pathological or neoplastic conditions.

In other embodiments, the cells may be used in the treatment of any kind of injury due to trauma, particularly trauma involving inflammation. Examples of such trauma-related conditions include central nervous system (CNS) injuries, including injuries to the brain, spinal cord, or tissue surrounding the CNS injuries to the peripheral nervous system (PNS); or injuries to any other part of the body. Such trauma may be caused by accident, or may be a normal or abnormal outcome of a medical procedure such as surgery or angioplasty. The trauma may be related to a rupture or occlusion of a blood vessel, for example, in stroke or phlebitis. In specific embodiments, the cells may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

In a specific embodiment, the disease or disorder is aplastic anemia, myelodysplasia, leukemia, a bone marrow disorder or a hematopoietic disease or disorder. In another specific embodiment, the subject is a human.

In another embodiment, the invention provides a method of treating an individual having a disease, disorder or condition associated with or resulting from inflammation. In other embodiments, the invention provides a method of treating an individual having a neurological disease, disorder or condition. In a more specific embodiment, said neurological disease is ALS. In another more specific embodiment, said neurological disease is Parkinson's disease. In another specific embodiment, said disease is a vascular or cardiovascular disease. In a more specific embodiment, said disease is atherosclerosis. In another specific embodiment, said disease is diabetes.

In a specific embodiment, the pharmaceutical compositions of the invention comprise an aliquot of umbilical cord blood to which embryonic-like placental stem cells have been added as disclosed above in Section 4.4.

A number of the embryonic-like stem cells, or of the supplemented cell populations, once administered, are able to engraft into the host, forming long-term "colonies." This results in a host that is essentially chimeric. Because chimeras in other genetic contexts are generally more vigorous and resilient, such chimerism is expected enhance the host's health and well-being. As such, the embryonic-like stem cells may be administered not simply to an individual suffering from a specific disease, disorder or condition, but may be administered to an individual in order to increase the individual's overall health and well-being.

The embryonic-like stem cells or supplemented cell populations of the invention may be treated prior to administration to an individual with compounds that modulate the activity of TNF-α. Such compounds are disclosed in detail in copending U.S. Provisional Application No. 60/372,348, filed Apr. 12, 2002, which disclosure is incorporated herein in its entirety. Preferred compounds are referred to as IMiDs and SelCids, and particularly preferred compounds are available under the trade names Actimid™ and Revimid™.

A particularly useful aspect of the embryonic-like stem cells of the invention is that, in certain embodiments, there is no need to HLA-type the cells prior to administration. In other words, embryonic-like stem cells may be taken from a heterologous donor, or a plurality of heterologous donors, and transplanted to an individual in need of such cells, and the transplanted cells will remain within the host indefinitely. This elimination of the need for HLA typing greatly facilitates both the transplantation procedure itself and the identification of donors for transplantation. However, the embryonic-like stem cells or supplemented cell populations containing them may be HLA matched (donor to recipient) prior to administration.

The inventors have discovered that the efficacy of treating an individual with the embryonic-like stem cells or supplemented cell populations is enhanced if these cells are preconditioned. Preconditioning comprises storing the cells in a gas-permeable container of a period of time at approximately −5 to 23° C., 0-10° C., or preferably 4-5° C. The period of time may be between 18 hours and 21 days, between 48 hours and 10 days, and is preferably between 3-5 days. The cells may be cryopreserved prior to preconditioning or, preferably, are preconditioned immediately prior to administration.

Thus, in one embodiment, the invention provides a method of treating an individual comprising administering to said individual embryonic-like stem cells collected from at least one donor. "Donor" as used herein means an adult, child, infant, or, preferably, a placenta. In another, preferred, embodiment, the method comprises administering to said individual embryonic-like stem cells that are collected from a plurality of donors and pooled. In a specific embodiment, said embryonic-like stem cells are stem cells taken from a plurality of donors. When collected form multiple donors, the dosage units, where a "dosage unit" is a collection from a single donor, may be pooled prior to administration, may be administered sequentially, or may be administered alternatively. In another embodiment of the method, said embryonic-like stem cells are mixed with, or "spiked" into umbilical cord blood, and the mixture administered to an individual. In more specific embodiments of the method, the ratio of embryonic-like stem cells to cord blood may be at least 20:80, 30:70, 40:60, 50:50, 60:40, 70:30 or 80:20, by number of total nucleated cells.

4.7 Administration of Stem Cells: Dosages

A particularly useful aspect of the invention is the administration of high doses of stem cells to an individual; such numbers of cells are significantly more effective than the material (for example, bone marrow or cord blood) from which they were derived. In this context, "high dose" indicates 5, 10, 15 or 20 or more times the number of total nucleated cells, including stem cells, particularly embryonic-like stem cells, than would be administered, for example, in a bone marrow transplant. Typically, a patient receiving a stem cell infusion, for example for a bone marrow transplantation, receives one unit of cells, where a unit is approximately $1 \times 10^9$ nucleated cells (corresponding to $1-2 \times 10^8$ stem cells). For high-dose therapies, therefore, a patient would be administered 3 billion, 5 billion, 10 billion, 15 billion, 20 billion, 30 billion, 40 billion, 50 billion or more, or, alternatively, 3, 5, 10, 20, 30, 40, or 50 units or more, of total nucleated cells, either embryonic-like stem cells alone, or embryonic-like stem cells spiked into another stem or progenitor cell population (e.g., embryonic-like stem cells spiked into umbilical cord blood). In one preferred embodiment, for example, an individual is given 15 units of spiked cord blood, where the unit contains approximately 750 million cord blood cells and 500 million embryonic-like stem cells. Thus, in one embodiment, the number of nucleated cells administered to an individual is at least five times the number of cells normally administered in a bone marrow replacement. In another specific embodiment of the method, the number of nucleated cells administered to an individual is at least ten times the number of cells normally administered in a bone marrow replacement. In another specific embodiment of the method, the number of nucleated cells administered to an individual is at least fifteen times the number of cells normally administered in a bone marrow replacement. In another embodiment of the method, the total number of nucleated cells, which includes stem cells, administered to an individual is between $1-100 \times 10^8$ per kilogram of body weight. In another embodiment, the number of total nucleated cells administered is at least 5 billion cells. In another embodiment, the total number of nucleated cells administered is at least 15 billion cells.

In another embodiment of the method, said embryonic-like stem cells and said cord blood are mixed immediately prior to (i.e., within five minutes of) administration to said individual. In another embodiment, said embryonic-like stem cells and said cord blood are mixed at a point in time more than five minutes prior to administration to said individual. In another embodiment of the method, the embryonic-like stem cells are cryopreserved and thawed prior to administration to said individual. In another embodiment, said embryonic-like stem cells and said cord blood are mixed to form a supplemented cell population at a point in time more than twenty-four hours prior to administration to said individual, wherein said supplemented cell population has been cryopreserved and thawed prior to said administration. In another embodiment, said embryonic-like stem cells and/or supplemented cell populations may be administered more than once. In another embodiment, said embryonic-like stem cells and/or supplemented cell populations are preconditioned by storage from between 18 hours and 21 days prior to administration. In a more specific embodiment, the cells are preconditioned for 48 hours to 10 days prior to administration. In a preferred specific embodiment, said cells are preconditioned for 3-5 days prior to transplantation. In a preferred embodiment of any of the methods herein, said embryonic-like stem cells are not HLA typed prior to administration to an individual.

In another specific embodiment of the method, said embryonic-like stem cells are primarily (i.e., >50%) CD34+ cells. In a more specific embodiment of the method, said embryonic-like stem cells are primarily CD34+33+ stem cells.

Therapeutic or prophylactic treatment of an individual with embryonic-like stem cells or supplemented cell populations containing them may be considered efficacious if the disease, disorder or condition is measurably improved in any way. Such improvement may be shown by a number of indicators. Measurable indicators include, for example, detectable changes in a physiological condition or set of physiological conditions associated with a particular disease, disorder or condition (including, but not limited to, blood pressure, heart rate, respiratory rate, counts of various blood cell types, levels in the blood of certain proteins, carbohydrates, lipids or cytokines or modulation expression of genetic markers associated with the disease, disorder or condition). Treatment of an individual with the stem cells or supplemented cell populations of the invention would be considered effective if any one of such indicators responds to such treatment by changing to a value that is within, or closer to, the normal value. The normal value may be established by normal ranges that are known in the art for various indicators, or by comparison to such values in a control. In medical science, the efficacy of a treatment is also often characterized in terms of an individual's impressions and subjective feeling of the individual's state of health. Improvement therefore may also be characterized by subjective indicators, such as the individual's subjective feeling of improvement, increased well-being, increased state of health, improved level of energy, or the like, after administration of the stem cells or supplemented cell populations of the invention.

The embryonic-like stem cells and supplemented cell populations of the invention may be administered to a patient in any pharmaceutically or medically acceptable manner, including by injection or transfusion. The cells or supplemented cell populations may be contain, or be contained in any pharmaceutically-acceptable carrier (See Section 4.8). The embryonic-like stem cells or supplemented cell populations may be carried, stored, or transported in any pharmaceutically or medically acceptable container, for example, a blood bag, transfer bag, plastic tube or vial.

4.7. Kits

The invention also provides a pharmaceutical pack or kit comprising one or more containers filled with one or more of the ingredients of the pharmaceutical compositions of the invention. Optionally associated with such container(s) can be: an apparatus for cell culture, one or more containers filled with a cell culture medium or one or more components of a cell culture medium, an apparatus for use in delivery of the compositions of the invention, e.g., an apparatus for the intravenous injection of the compositions of the invention, and/or a notice in the form prescribed by a governmental agency regulating the manufacture, use or sale of pharmaceuticals or biological products, which notice reflects approval by the agency of manufacture, use or sale for human administration. In a specific embodiment, the kit comprises one or more containers filled with embryonic-like stem cells of the invention and one or more different containers filled with stem cells, e.g., umbilical cord blood, as disclosed above.

In one embodiment, the kit comprises a mixture of stem cells, e.g., cord blood cells, supplemented with embryonic-like stem cells contained within one bag or container. In another embodiment, the kit comprises a population of cord blood cells and a population of embryonic-like stem cells that are contained within two separate bags or containers. In certain embodiments, the kit comprises a "two bag" composition wherein the bag containing the cord blood cells and the bag containing the embryonic-like stem cells is mixed prior to, or at the time of, administration to a patient in need thereof. In other embodiments, the kit comprises a population of cord blood cells and a population of embryonic-like stem cells that are contained within two separate bags or containers and that are administered separately (e.g., simultaneously or sequentially) to a patient, wherein the mixing of the two cell populations occurs in vivo.

In another embodiment, the kit provides a population of cord blood cells and a population of embryonic-like stem cells that are physically mixed prior to administration. In another aspect of this embodiment, the kit comprises a container containing a growth factor, e.g., GM-CSF, IL-4, Flt3L, CD40L, IFN-alpha, TNF-alpha, IFN-gamma, IL-2, IL-6, retinoic acid, basic fibroblast growth factor, TGF-beta-1, TGF-beta-3, hepatocyte growth factor, epidermal growth factor, cardiotropin-1, angiotensinogen, angiotensin I (AI), angiotensin II (AII), AII $AT_2$ type 2 receptor agonists, or analogs or fragments thereof. In another aspect of this embodiment, the two populations are physically mixed and then treated with the growth factor comprised in the kit, to induce cell differentiation, prior to administration to the patient. In another aspect of this embodiment, the cord blood cells and/or the embryonic-like stem cells are treated with the growth factor comprised in the kit, to induce cell differentiation and then physically mixed prior to administration to the patient.

The following experimental examples are offered by way of illustration and not by way of limitation.

5. EXAMPLES

5.1. Example 1

Analysis of Cell Types Recovered from Perfusate of Drained Placenta

This example describes the analysis of the cell types recovered from the effluent perfusate of a placenta cultured according to the methods of the invention.

Twenty ml of phosphate buffered saline solution (PBS) was added to the perfusion liquid and a 10 ml portion was collected and centrifuged for 25 minutes at 3000 rpm (revolutions per minute). The effluent was divided into four tubes and placed in an ice bath. 2.5 ml of a 1% fetal calf serum (FCS) solution in PBS was added and the tubes were centrifuged (140 minutes×10 g (acceleration due to gravity)). The pellet was resuspended in 5 ml of 1% FCS and two tubes were combined. The total mononucleocytes were calculated by adding the total lymphocytes and the total monocytes, and then multiplying the result by the total cell suspension volume.

The following table discloses the types of cells obtained by perfusion of a cultured placenta according to the methods described hereinabove.

|  | WBC 1000/ml | Lym % | MID % | GRA % | Total Volume | # of Cells |
|---|---|---|---|---|---|---|
| CB (Cord Blood) | 10.5 | 43.2 | 8 | 48.8 | 60 ml | $6.3 \times 10^8$ |
| PP (Placenta perfusate, room temperature) | 12.0 | 62.9 | 18.2 | 18.9 | 15 ml | $1.8 \times 10^8$ |
| $PP_2$ (Placenta perfusate, 37° C.) | 11.7 | 56.0 | 19.2 | 24.8 | 30 ml | $3.5 \times 10^8$ |

Samples of PP were after Ficoll.
Total cell number of PP after Ficoll was $5.3 \times 10^8$ and number of CB before processing is $6.3 \times 10^8$. Lym % indicates percent of lymphocytes; MID % indicates percent of midrange white blood cells; and GRA % indicates percent of granulocytes.

5.2. Example 2

Analysis of Cells Obtained by Perfusion and Incubation of Placenta

The following example describes an analysis of cells obtained by perfusion and incubation of placenta according to the methods of the invention.

5.2.1. Materials and Methods

Placenta donors were recruited from expectant mothers that enrolled in private umbilical cord blood banking programs and provided informed consent permitting the use of the exsanguinated placenta following recovery of cord blood for research purposes. Donor data may be confidential. These donors also permitted use of blinded data generated from the normal processing of their umbilical cord blood specimens for cryopreservation. This allowed comparison between the composition of the collected cord blood and the effluent perfusate recovered using the experimental method described below.

Following exsanguination of cord blood from the umbilical cord and placenta is stored at room temperature and delivered to the laboratory within four to twenty-four hour, according to the methods described hereinabove, the placenta was placed in a sterile, insulated container at room temperature and delivered to the laboratory within 4 hours of birth. Placentas were discarded if, on inspection, they had evidence of physical damage such as fragmentation of the organ or avulsion of umbilical vessels. Placentas were maintained at room temperature (23±2° C.) or refrigerated (4° C.) in sterile containers for 2 to 20 hours. Periodically, the placentas were immersed and washed in sterile saline at 25±3° C. to remove any visible surface blood or debris.

The umbilical cord was transected approximately 5 cm from its insertion into the placenta and the umbilical vessels were cannulated with TEFLON® or polypropylene catheters connected to a sterile fluid path allowing bi-directional perfusion of the placenta and recovery of the effluent fluid. The methods described hereinabove enabled all aspects of placental conditioning, perfusion and effluent collection to be performed under controlled ambient atmospheric conditions as well as real-time monitoring of intravascular pressure and flow rates, core and perfusate temperatures and recovered effluent volumes. A range of conditioning protocols were evaluated over a 24-hour postpartum period, and the cellular composition of the effluent fluid was analyzed by flow cytometry, light microscopy and colony forming unit assays.

5.2.2. Placental Conditioning

The donor placentas were processed at room temperature within 12 to 24 hours after delivery. Before processing, the membranes were removed and the maternal site washed clean of residual blood. The umbilical vessels were cannulated with catheters made from 20 gauge Butterfly needles use for blood sample collection.

The donor placentas were maintained under varying conditions such as maintenance at 5-37° 5% $CO_2$, pH 7.2 to 7.5, preferably pH 7.45, in an attempt to simulate and sustain a physiologically compatible environment for the proliferation and recruitment of residual embryonic-like stem cells. The cannula was flushed with IMDM serum-free medium (GibcoBRL, NY) containing 2U/ml heparin (Elkins-Sinn, N.J.). Perfusion of the placenta continued at a rate of 50 ml per minute until approximately 150 ml of perfusate was collected. This volume of perfusate was labeled "early fraction." Continued perfusion of the placenta at the same rate resulted in the collection of a second fraction of approximately 150 ml and was labeled "late fraction." During the course of the procedure, the placenta was gently massaged to aid in the perfusion process and assist in the recovery of cellular material. Effluent fluid was collected from the perfusion circuit by both gravity drainage and aspiration through the arterial cannula.

Placentas were then perfused with heparinized (2U/ml) Dulbecco's modified Eagle Medium (H.DMEM) at the rate of 15 ml/minute for 10 minutes and the perfusates were collected from the maternal sites within one hour and the nucleated cells counted. The perfusion and collection procedures were repeated once or twice until the number of recovered nucleated cells fell below 100/ml. The perfusates were pooled and subjected to light centrifugation to remove platelets, debris and de-nucleated cell membranes. The nucleated cells were then isolated by Ficoll-Hypaque density gradient centrifugation and after washing, resuspended in H.DMEM. For isolation of the adherent cells, aliquots of $5-10 \times 10^6$ cells were placed in each of several T-75 flasks and cultured with commercially available Mesenchymal Stem Cell Growth Medium (MSCGM) obtained from BioWhittaker, and placed in a tissue culture incubator (37° C., 5% $CO_2$). After 10 to 15 days, the non-adherent cells were removed by washing with PBS, which was then replaced by MSCGM. The flasks were examined daily for the presence of various adherent cell types and in particular, for identification and expansion of clusters of fibroblastoid cells.

5.2.3. Cell Recovery and Isolation

Cells were recovered from the perfusates by centrifugation at 5000×g for 15 minutes at room temperature. This procedure served to separate cells from contaminating debris and platelets. The cell pellets were resuspended in IMDM serum-free medium containing 2U/ml heparin and 2 mM EDTA (GibcoBRL, NY). The total mononuclear cell fraction was isolated using Lymphoprep (Nycomed Pharma, Oslo, Norway) according to the manufacturer's recommended procedure and the mononuclear cell fraction was resuspended. Cells were counted using a hemocytometer. Viability was evaluated by trypan blue exclusion. Isolation of mesenchymal cells was achieved by "differential trypsinization," using a solution of 0.05% trypsin with 0.2% EDTA (Sigma, St. Louis Mo.). Differential trypsinization was possible because fibroblastoid cells detached from plastic surfaces within about five minutes whereas the other adherent populations required more than 20-30 minutes incubation. The detached fibroblastoid cells were harvested following trypsinization and trypsin neutralization, using Trypsin Neutralizing Solution (TNS, BioWhittaker). The cells were washed in H.DMEM and resuspended in MSCGM.

Flow cytometry was carried out using a Becton-Dickinson FACSCalibur instrument and FITC and PE labeled monoclonal antibodies (mAbs), selected on the basis of known markers for bone marrow-derived MSC (mesenchymal stem cells), were purchased from B. D. and Caltag laboratories (South San Francisco, Calif.), and SH2, SH3 and SH4 antibody producing hybridomas were obtained from and reactivities of the mAbs in their cultured supernatants were detected by FITC or PE labeled $F(ab)'^2$ goat anti-mouse antibodies. Lineage differentiation was carried out using commercially available induction and maintenance culture media (BioWhittaker), used as per manufacturer's instructions.

5.2.4. Isolation of Placental Embryonic-Like Stem Cells

Microscopic examination of the adherent cells in the culture flasks revealed morphologically different cell types. Spindle-shaped cells, round cells with large nuclei and numerous perinuclear small vacuoles, and star-shaped cells with several projections (through one of which star-shaped cells were attached to the flask) were observed adhering to the culture flasks. Although no attempts were made to further characterize these adherent cells, similar cells were observed in the culture of bone marrow, cord and peripheral blood, and therefore considered to be non-stem cell-like in nature. The fibroblastoid cells, appearing last as clusters, were candidates for being MSC (mesenchymal stem cells) and were isolated by differential trypsinization and subcultured in secondary flasks. Phase microscopy of the rounded cells, after trypsinization, revealed that the cells were highly granulated; indistinguishable from the bone marrow-derived MSC produced in the laboratory or purchased from BioWhittaker. When subcultured, the placenta-derived embryonic-like stem cells, in contrast to their earlier phase, adhered within hours, assumed characteristic fibroblastoid shape, and formed a growth pattern identical to the reference bone marrow-derived MSC. During subculturing and refeeding, moreover, the loosely bound mononuclear cells were washed out and the cultures remained homogeneous and devoid of any visible non-fibroblastoid cell contaminants.

5.2.5. Results

The expression of CD-34, CD-38, and other stem cell-associated surface markers on early and late fraction purified mononuclear cells was assessed by flow cytometry. Recovered, sorted cells were washed in PBS and then double-stained with antiCD34 phycoerythrin and anti-CD38 fluorescein isothiocyanate (Becton Dickinson, Mountain View, Calif.).

Cell isolation was achieved by using magnetic cell separation, such as for example, Auto Macs (Miltenyi). Preferably, CD 34+ cell isolation is performed first.

5.3. Example 3

Perfusion Medium

The following example provides a formula of the preferred perfusate solution for the cultivation of isolated placentas.

| Chemical | Source | Stock Concentration | Final Concentration | 500 ml |
|---|---|---|---|---|
| DMEM-LG | GibcoBRL11885-084 | | | 300 ml |
| MCDB201 | Sigma M-6770 | dissolved in H2O | pH to 7.2. filter | 200 ml |
| FCS | Hyclone | 100% | 2% | 10 ml |
| ITS | Sigma I-3146 or GibcoBRL41400-045 | 100x | 1x | 5 ml |
| Pen & Strep | GibcoBRL15140-122 | 100x | 1x | 5 ml |
| LA + BSA | Sigma + GibcoBRL BSA | 100x(1 µg/ml of LA | 10 ng/ml of LA | 5 ml |
| Dexamethasone | Sigma D-2915 | 0.25 mM in H2O | 0.05 µM | 100 µl |
| L-Ascorbic Acid | Sigma A-8960 | 1000x(100 mM) | 1x(0.1 mM) | 500 µl |

-continued

| Chemical | Source | Stock Concentration | Final Concentration | 500 ml |
|---|---|---|---|---|
| PDGF (50 μg) | R&D 220BD | 10 μg/ml in 4 mM HCl + 0.1% BSA | 10 ng/ml | 500 μl |
| EGF (200 μg) | Sigma E-9644 | 10 μg/ml in 10 mM HAc + 0.1% BSA | 10 ng/ml | 500 μl |

The above-composition is a perfusate that may be used at a variety of temperatures to perfuse placenta. It should be noted that additional components such as antibiotics, anticoagulant and other growth factors may be used in the perfusate or culture media.

5.4 Example 4

Induction of Differentiation into Particular Cell Types

Cord blood cells and/or embryonic-like stem cells are induced to differentiate into a particular cell type by exposure to a growth factor. Growth factors that are used to induce induction include, but are not limited to: GM-CSF, IL-4, Flt3L, CD40L, IFN-alpha, TNF-alpha, IFN-gamma, IL-2, IL-6, retinoic acid, basic fibroblast growth factor, TGF-beta-1, TGF-beta-3, hepatocyte growth factor, epidermal growth factor, cardiotropin-1, angiotensinogen, angiotensin I (AI), angiotensin II (AII), AII $AT_2$ type 2 receptor agonists, or analogs or fragments thereof.

5.4.1 Induction Of Differentiation Into Neurons

This example describes the induction of cord blood cells and/or embryonic-like stem cells to differentiate into neurons. The following protocol is employed to induce neuronal differentiation:

1. Placental stem cells are grown for 24 hr in preinduction media consisting of DMEM/20% FBS and 1 mM beta-mercaptoethanol.
2. Preinduction media is removed and cells are washed with PBS.
3. Neuronal induction media consisting of DMEM and 1-10 mM betamercaptoethanol is added. Alternatively, induction media consisting of DMEM/2% DMSO/200 μM butylated hydroxyanisole may be used to enhance neuronal differentiation efficiency.
4. In certain embodiments, morphologic and molecular changes may occur as early as 60 minutes after exposure to serum-free media and betamercaptoethanol (Woodbury et al., J. Neurosci. Res., 61:364-370). RT/PCR may be used to assess the expression of e.g., nerve growth factor receptor and neurofilament heavy chain genes.

5.4.2 Induction Of Differentiation Into Adipocytes

This example describes the induction of cord blood cells and/or embryonic-like stem cells to differentiate into adipocytes. The following protocol is employed to induce adipogenic differentiation:

1. Placental stem cells are grown in MSCGM (Bio Whittaker) or DMEM supplemented with 15% cord blood serum.
2. Three cycles of induction/maintenance are used. Each cycle consists of feeding the placental stem cells with Adipogenesis Induction Medium (Bio Whittaker) and culturing the cells for 3 days (at 37° C., 5% $CO_2$), followed by 1-3 days of culture in Adipogenesis Maintenance Medium (Bio Whittaker). An induction medium is used that contains 1 μM dexamethasone, 0.2 mM indomethacin, 0.01 mg/ml insulin, 0.5 mM IBMX, DMEM-high glucose, FBS, and antibiotics.
3. After 3 complete cycles of induction/maintenance, the cells are cultured for an additional 7 days in adipogenesis maintenance medium, replacing the medium every 2-3 days.
4. Adipogenesis may be assessed by the development of multiple intracytoplasmic lipid vesicles that can be easily observed using the lipophilic stain oil red O. RT/PCR assays are employed to examine the expression of lipase and fatty acid binding protein genes.

5.4.3 Induction of Differentiation into Chondrocytes

This example describes the induction of cord blood cells and/or embryonic-like stem cells to differentiate into chondrocytes. The following protocol is employed to induce chondrogenic differentiation:

1. Placental stem cells are maintained in MSCGM (Bio Whittaker) or DMEM supplemented with 15% cord blood serum.
2. Placental stem cells are aliquoted into a sterile polypropylene tube. The cells are centrifuged (150×g for 5 minutes), and washed twice in Incomplete Chondrogenesis Medium (Bio Whittaker).
3. After the last wash, the cells are resuspended in Complete Chondrogenesis Medium (Bio Whittaker) containing 0.01 μg/ml TGF-beta-3 at a concentration of 5×10(5) cells/ml.
4. 0.5 ml of cells is aliquoted into a 15 ml polypropylene culture tube. The cells are pelleted at 150×g for 5 minutes. The pellet is left intact in the medium.
5. Loosely capped tubes are incubated at 37° C., 5% $CO_2$ for 24 hours.
6. The cell pellets are fed every 2-3 days with freshly prepared complete chondrogenesis medium.
7. Pellets are maintained suspended in medium by daily agitation using a low speed vortex.
8. Chondrogenic cell pellets are harvested after 14-28 days in culture.
9. Chondrogenesis may be characterized by e.g., observation of production of esoinophilic ground substance, assessing cell morphology, an/or RT/PCR for examining collagen 2 and collagen 9 gene expression.

5.4.4 Induction of Differentiation into Osteocytes

This example describes the induction of cord blood cells and/or embryonic-like stem cells to differentiate into osteocytes. The following protocol is employed to induce osteogenic differentiation:

1. Adherent cultures of placental stem cells are cultured in MSCGM (Bio Whittaker) or DMEM supplemented with 15% cord blood serum.
2. Cultures are rested for 24 hours in tissue culture flasks.

3. Osteogenic differentiation is induced by replacing MSCGM with Osteogenic Induction Medium (Bio Whittaker) containing 0.1 µM dexamethasone, 0.05 mM ascorbic acid-2-phosphate, 10 mM beta glycerophosphate.
4. Cells are fed every 3-4 days for 2-3 weeks with Osteogenic Induction Medium.
5. Differentiation is assayed using a calcium-specific stain and RT/PCR for alkaline phosphatase and osteopontin gene expression.

5.4.5 Induction Of Differentiation Into Hepatocytes

This example describes the induction of cord blood cells and/or embryonic-like stem cells to differentiate into hepatocytes. The following protocol is employed to induce hepatogenic differentiation:
1. Placental stem cells are cultured in DMEM/20% CBS supplemented with hepatocyte growth factor, 20 ng/ml; and epidermal growth factor, 100 ng/ml. KnockOut Serum Replacement may be used in lieu of FBS.
2. IL-6 50 ng/ml is added to induction flasks.

5.4.6 Induction of Differentiation into Pancreatic Cells

This example describes the induction of cord blood cells and/or embryonic-like stem cells to differentiate into pancreatic cells. The following protocol is employed to induce pancreatic differentiation:
1. Placental stem cells are cultured in DMEM/20% CBS, supplemented with basic fibroblast growth factor, 10 ng/ml; and transforming growth factor beta-1, 2 ng/ml. KnockOut Serum Replacement may be used in lieu of CBS.
2. Conditioned media from nestin-positive neuronal cell cultures is added to media at a 50/50 concentration.
3. Cells are cultured for 14-28 days, refeeding every 3-4 days.
4. Differentiation is characterized by assaying for insulin protein or insulin gene expression by RT/PCR.

5.4.7 Induction of Differentiation into Cardiac Cells

This example describes the induction of cord blood cells and/or embryonic-like stem cells to differentiate into cardiac cells. The following protocol is employed to induce myogenic differentiation:
1. Placental stem cells are cultured in DMEM/20% CBS, supplemented with retinoic acid, 1 µM; basic fibroblast growth factor, 10 ng/ml; and transforming growth factor beta-1, 2 ng/ml; and epidermal growth factor, 100 ng/ml. KnockOut Serum Replacement may be used in lieu of CBS.
2. Alternatively, placental stem cells are cultured in DMEM/20% CBS supplemented with 50 ng/ml Cardiotropin-1 for 24 hours.
3. Alternatively, placental stem cells are maintained in protein-free media for 5-7 days, then stimulated with human myocardium extract (escalating dose analysis). Myocardium extract is produced by homogenizing 1 gm human myocardium in 1% HEPES buffer supplemented with 1% cord blood serum. The suspension is incubated for 60 minutes, then centrifuged and the supernatant collected.
4. Cells are cultured for 10-14 days, refeeding every 3-4 days.
5. Differentiation is assessed using cardiac actin RT/PCR gene expression assays.

5.4.8 Characterization of Cord Blood Cells and/or Embryonic-Like Stem Cells Prior to and/or After Differentiation The embryonic-like stem cells, the cord blood cells and/or the populations of cord blood cells spiked with embryonic-like stem cells are characterized prior to and/or after differentiation by measuring changes in morphology and cell surface markers using techniques such as flow cytometry and immunocytochemistry, and measuring changes in gene expression using techniques, such as PCR. Cells that have been exposed to growth factors and/or that have differentiated are characterized by the presence or absence of the following cell surface markers: CD10+, CD29+, CD34−, CD38−, CD44+, CD45−, CD54+, CD90+, SH2+, SH3+, SH4+, SSEA3−, SSEA4−, OCT-4+, and ABC-p+. Preferably, the embryonic-like stem cell are characterized, prior to differentiation, by the presence of cell surface markers OCT-4+, APC-p+, CD34− and CD38−. Stem cells bearing these markers are as versatile (e.g., pluripotent) as human embryonic stem cells. Cord blood cells are characterized, prior to differentiation, by the presence of cell surface markers CD34+ and CD38+. Differentiated cells derived from embryonic-like stem cells, cord blood cells and/or a populations of cord blood cells spiked with embryonic-like stem cells preferably do not express these markers.

5.5 Example 5

Treatment of Individuals Having Amylotrophic Lateral Sclerosis with Embryonic-Like Stem Cells Amyotrophic Lateral Sclerosis (ALS), also called Lou Gehrig's disease, is a fatal neurodegenerative disease affecting motor neurons of the cortex, brain stem and spinal cord. ALS affects as many as 20,000 Americans with 5,000 new cases occurring in the US each year. The majority of ALS cases are sporadic (S-ALS) while 5-10% are hereditary (familial—F-ALS). ALS occurs when specific nerve cells in the brain and spinal cord that control voluntary movement gradually degenerate. The cardinal feature of ALS is the loss of spinal motor neurons which causes the muscles under their control to weaken and waste away leading to paralysis. ALS manifests itself in different ways, depending on which muscles weaken first. ALS strikes in mid-life with men being one-and-a-half times more likely to have the disease as women. ALS is usually fatal within five years after diagnosis.

ALS has both familial and sporadic forms, and the familial forms have now been linked to several distinct genetic loci. Only about 5-10% of ALS cases are familial. Of these, 15-20% are due to mutations in the gene encoding Cu/Zn superoxide dismutase 1 (SOD1). These appear to be "gain-of-function" mutations that confer toxic properties on the enzyme. The discovery of SOD mutations as a cause for ALS has paved the way for some progress in the understanding of the disease; animal models for the disease are now available and hypotheses are being developed and tested concerning the molecular events leading to cell death.

Presented below is an example method of treating an individual having ALS with embryonic-like stem cells derived from placenta. The method involves intravenous infusion through a peripheral, temporary angiocatheter.

An individual having ALS is first assessed by the performance of standard laboratory analyses. Such analyses may include a metabolic profile; CDC with differential; lipid profile; fibrinogen level; ABO rH typing of the blood; liver function tests; and determination of BUN/creatine levels. Individuals are instructed the day prior to the transplant to take the following medications: diphenhydramine (Benadryl™), 25 mg t.i.d, and prednisone, 10 mg.

The embryonic-like stem cells, either alone or spiked into cord blood, are taken from cryopreserved stock, thawed, and maintained for approximately two days prior to transplantation at a temperature of approximately 5° C.

The individual is transplanted at an outpatient clinical center which has all facilities necessary for intravenous infusion, physiological monitoring and physical observation. Approximately one hour prior to transplantation, the individual receives diphenhydramine (Benadryl™), 25 mg×1 P.O., and prednisone, 10 mg×1 P.O. This is precautionary, and is meant to reduce the likelihood of an acute allergic reaction. At the time of transfusion, an 18 G indwelling peripheral venous line is places into one of the individual's extremities, and is maintained open by infusion of D5 ½ normal saline +20 mEq KCl at a TKO rate. The individual is examined prior to transplantation, specifically to note heart rate, respiratory rate, temperature. Other monitoring may be performed, such as an electrocardiogram and blood pressure measurement.

Embryonic-like stem cells are then infused at a rate of 1 unit per hour in a total delivered fluid volume of 60 ml, where a unit is approximately 1-2 $10^9$ total nucleated cells. Alternatively, the unit of embryonic-like stem cells is delivered in cord blood having a total fluid volume of 60 ml. In this case, the ratio of the number of embryonic-like stem cells to stem cells in the cord blood is at least 2:1. The administered unit may also consist of cord blood alone. Based upon data from pre-clinical studies in mice, a total of $2.0\text{-}2.5\times10^8$ cells per kilogram of body weight should be administered. For example, a 70 kilogram individual would receive approximately $14\text{-}18\times10^9$ total nucleated cells. The individual should be monitored for signs of allergic response or hypersensitivity, which are signals for immediate cessation of infusion.

Post-infusion, the individual should be monitored in a recumbent position for at least 60 minutes, whereupon he or she may resume normal activities.

5.6 Example 6

Treatment of Individuals Having Atherosclerosis Using Embryonic-Like Stem Cells

The infusion protocol outlined in Example 5 may be used to administer the embryonic-like stem cells, either alone or spiked into umbilical cord blood, to a patient having atherosclerosis. The embryonic-like stem cells or supplemented cell populations may be administered to asymptomatic individuals, individuals that are candidates for angioplasty, or to patients that have recently (within one week) undergone cardiac surgery.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A composition comprising human stem or progenitor cells and isolated human placental stem cells that are $SH2^+$, $SH3^+$, $SH4^+$ and $OCT\text{-}4^+$, wherein said placental stem cells are obtained from a placenta that has been drained of cord blood and flushed to remove residual blood.

2. A composition comprising human umbilical cord blood cells and isolated human placental stem cells that are $SH2^+$, $SH3^+$, $SH4^+$ and $OCT\text{-}4^+$, wherein said placental stem cells are obtained from a placenta that has been drained of cord blood and flushed to remove residual blood.

3. A composition comprising human stem or progenitor cells and isolated human placental stem cells that are $SH2^+$, $SH3^+$, $SH4^+$, $SSEA3^-$ and $SSEA4^-$, wherein said placental stem cells are obtained from a placenta that has been drained of cord blood and flushed to remove residual blood.

4. A composition comprising human umbilical cord blood cells and isolated human placental stem cells that are $SH2^+$, $SH3^+$, $SH4^+$, $SSEA3^-$ and $SSEA4^-$, wherein said placental stem cells are obtained from a placenta that has been drained of cord blood and flushed to remove residual blood.

5. The composition of any of claim 1, 2, 3 or 4 that is contained in a container.

6. The composition of claim 5 wherein the container is sealed, air tight, and sterile.

7. The composition of claim 1 or claim 3 wherein the stem or progenitor cells are from umbilical cord blood or placental blood, fetal or neonatal hematopoietic stem or progenitor cells, adult cells or bone marrow stem or progenitor cells.

8. The composition of claim 7 wherein the stem or progenitor cells are fetal or neonatal hematopoietic stem or progenitor cells.

9. The composition of claim 8 wherein a plurality of the hematopoietic stem or progenitor cells are $CD34^+$ and $CD38^-$.

10. The composition of claim 2 or claim 4 wherein a plurality of the umbilical cord blood stem cells are $CD34^+$ and $CD38^+$.

11. The composition of claim 2 or claim 4 wherein a plurality of the umbilical cord blood stem cells are $CD34^+$ and $CD38^+$.

12. The composition of claim 1 or 2 wherein the placental stem cells exhibit at least one of the following cell surface markers: CD10, CD29, CD44, CD54, or CD90, or lack at least one of the following cell surface markers: CD34, CD45, SSEA3, or SSEA4.

13. A kit comprising a composition of claim 1 or 3 wherein said stem or progenitor cells are in a first container and said placental stem cells are in a second container.

14. A composition which comprises human stem or progenitor cells from umbilical cord blood supplemented with a plurality of isolated human placental stem cells that are $SH2^+$, $SH3^+$, $SH4^+$ and $OCT\text{-}4^+$, wherein said placental stem cells are obtained from a placenta that has been drained of cord blood and flushed to remove residual blood, and wherein the ratio of placental stem cells to said stem or progenitor cells is at least 1:1 in numbers.

15. The composition of claim 3 or 4 wherein the placental stem cells exhibit at least one of the following cell surface markers: CD10, CD29, CD44, CD54, CD90, or OCT-4, or lack at least one of the following cell surface markers: CD34 or CD45.

16. A kit comprising a composition of claim 2 or claim 4 wherein said umbilical cord blood cells are in a first container and said placental stem cells are in a second container.

17. A composition which comprises a number of human stem or progenitor cells from umbilical cord blood supplemented with a number of isolated human placental stem cells that are $SH2^+$, $SH3^+$, $SH4^+$, $SSEA3^-$ and $SSEA4^{31}$, wherein said placental stem cells are obtained from a placenta that has been drained of cord blood and flushed to remove residual blood, and wherein the ratio of the number of placental stem cells to the number of said stem or progenitor cells is at least 1:1.

* * * * *

UNITED STATES PATENT AND TRADEMARK OFFICE
CERTIFICATE OF CORRECTION

PATENT NO. : 7,311,905 B2  Page 1 of 1
APPLICATION NO. : 10/366671
DATED : December 25, 2007
INVENTOR(S) : Robert J. Hariri It is certified that error appears in the above-identified patent and that said Letters Patent is hereby corrected as shown below:

Column 40, line 27, replace "CD38+" with --CD38$^-$--

Column 40, line 58, replace "SSEA4$^{31}$" with --SSEA4$^-$--

Signed and Sealed this

Twenty Second Day of April, 2008

JON W. DUDAS
*Director of the United States Patent and Trademark Office*